US012690801B2

(12) United States Patent
Zhang et al.

(10) Patent No.: US 12,690,801 B2
(45) Date of Patent: Jul. 28, 2026

(54) METHODS AND SYSTEMS FOR DETERMINING AND USING AN INTENSITY INDEX FOR ELECTRICAL STIMULATION

(71) Applicant: Boston Scientific Neuromodulation Corporation, Valencia, CA (US)

(72) Inventors: Tianhe Zhang, Studio City, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 869 days.

(21) Appl. No.: 18/075,802

(22) Filed: Dec. 6, 2022

(65) Prior Publication Data

US 2023/0181089 A1     Jun. 15, 2023

Related U.S. Application Data

(60) Provisional application No. 63/288,357, filed on Dec. 10, 2021.

(51) Int. Cl.
*A61B 5/383* (2021.01)
*A61B 5/00* (2006.01)

(52) U.S. Cl.
CPC ............ *A61B 5/383* (2021.01); *A61B 5/7246* (2013.01)

(58) Field of Classification Search
None
See application file for complete search history.

(56) References Cited

U.S. PATENT DOCUMENTS

| | | |
|---|---|---|
| 3,999,555 A | 12/1976 | Person |
| 4,144,889 A | 3/1979 | Tyers et al. |
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |

(Continued)

FOREIGN PATENT DOCUMENTS

| | | |
|---|---|---|
| EP | 0813889 | 12/1997 |
| EP | 1048320 | 11/2000 |

(Continued)

OTHER PUBLICATIONS

Nowinski, W. L., et al., "Statistical analysis of 168 bilateral subthalamic nucleus implantations by means of the probabilistic functional atlas.", Neurosurgery 57(4 Suppl) (Oct. 2005),319-30.

(Continued)

*Primary Examiner* — Jay B Shah

(74) *Attorney, Agent, or Firm* — Branch Partners PLLC; Bruce E. Black

(57) ABSTRACT

A method for determining an intensity index for electrical stimulation includes receiving stimulation information; determining a stimulation field from the stimulation information; determining at least one stimulation field function using the stimulation field; and analyzing the determined at least one stimulation field function to determine the intensity index. The intensity index corresponds to a stimulation target and indexes at least one dosing reference for electrical stimulation for that stimulation target.

17 Claims, 3 Drawing Sheets

(56) References Cited

U.S. PATENT DOCUMENTS

| | | |
|---|---|---|
| 5,255,693 A | 10/1993 | Dutcher |
| 5,259,387 A | 11/1993 | dePinto |
| 5,304,206 A | 4/1994 | Baker et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulman |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,792,205 A | 8/1998 | Alt et al. |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Aw et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,080,187 A | 6/2000 | Alt et al. |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,721,603 B2 | 4/2004 | Zabara et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 6,993,384 B2 | 1/2006 | Bradley et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,518 B2 | 11/2006 | Griffin et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,203,548 B2 | 4/2007 | Whitehurst et al. |
| 7,209,787 B2 | 4/2007 | Dilorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |

(56) References Cited

U.S. PATENT DOCUMENTS

| | | |
|---|---|---|
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,289,761 B2 | 10/2007 | Mazar |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,282 B2 | 3/2008 | Sakanaka et al. |
| 7,346,382 B2 | 3/2008 | Mcintyre et al. |
| 7,385,443 B1 | 6/2008 | Denison |
| 7,388,974 B2 | 6/2008 | Yanagita |
| 7,437,193 B2 | 10/2008 | Parramon et al. |
| 7,450,997 B1 | 11/2008 | Pianca et al. |
| 7,454,245 B2 | 11/2008 | Armstrong et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,596,414 B2 | 9/2009 | Whitehurst et al. |
| 7,603,177 B2 | 10/2009 | Sieracki et al. |
| 7,610,103 B2 | 10/2009 | Whitehurst et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,896,808 B1 | 3/2011 | Koh et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,000,794 B2 | 8/2011 | Lozano |
| 8,019,439 B2 | 9/2011 | Kuzma et al. |
| 8,019,443 B2 | 9/2011 | Schleicher et al. |
| 8,175,710 B2 | 5/2012 | He |
| 8,180,601 B2 | 5/2012 | Butson et al. |
| 8,187,209 B1 | 5/2012 | Giuffrida |
| 8,195,300 B2 | 6/2012 | Gliner et al. |
| 8,209,027 B2 | 6/2012 | Butson et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,306,627 B2 | 11/2012 | Armstrong |
| 8,326,433 B2 | 12/2012 | Blum et al. |
| 8,359,107 B2 | 1/2013 | Pianca et al. |
| 8,364,278 B2 | 1/2013 | Pianca et al. |
| 8,369,954 B2 | 2/2013 | Stack et al. |
| 8,379,952 B2 | 2/2013 | Mcintyre et al. |
| 8,391,985 B2 | 3/2013 | McDonald |
| 8,412,349 B2 | 4/2013 | Barker |
| 8,429,174 B2 | 4/2013 | Ramani et al. |
| 8,452,415 B2 | 5/2013 | Goetz et al. |
| 8,467,883 B2 | 6/2013 | Chen et al. |
| 8,473,061 B2 | 6/2013 | Moffitt et al. |
| 8,483,237 B2 | 7/2013 | Zimmermann et al. |
| 8,543,189 B2 | 9/2013 | Paitel et al. |
| 8,571,665 B2 | 10/2013 | Moffitt et al. |
| 8,589,316 B2 | 11/2013 | Lujan et al. |
| 8,594,800 B2 | 11/2013 | Butson et al. |
| 8,594,801 B2 | 11/2013 | Corndorf et al. |
| 8,606,360 B2 | 12/2013 | Butson et al. |
| 8,620,452 B2 | 12/2013 | King et al. |
| 8,649,845 B2 | 2/2014 | McIntyre et al. |
| 8,675,945 B2 | 3/2014 | Barnhorst et al. |
| 8,679,038 B1 | 3/2014 | Giuffrida |
| 8,688,235 B1 | 4/2014 | Pianca et al. |
| 8,744,596 B2 | 6/2014 | Howard |
| 8,751,008 B2 | 6/2014 | Carlton et al. |
| 8,751,016 B2 | 6/2014 | Schleicher et al. |
| 8,774,941 B2 | 7/2014 | Pianca |
| 8,792,993 B2 | 7/2014 | Pianca et al. |
| 8,831,731 B2 | 9/2014 | Blum et al. |
| 8,831,742 B2 | 9/2014 | Pianca et al. |
| 8,845,557 B1 | 9/2014 | Giuffrida et al. |
| 8,849,632 B2 | 9/2014 | Sparks et al. |
| 8,855,773 B2 | 10/2014 | Kokones et al. |
| 8,868,199 B2 | 10/2014 | Kaula et al. |
| 8,913,804 B2 | 12/2014 | Blum et al. |
| 8,918,183 B2 | 12/2014 | Carlton et al. |
| 8,918,184 B1 | 12/2014 | Torgerson et al. |
| 8,923,976 B2 | 12/2014 | Johanek |
| 8,936,622 B2 | 1/2015 | Wales et al. |
| 8,958,615 B2 | 2/2015 | Blum et al. |
| 8,972,023 B2 | 3/2015 | Bradley et al. |
| 8,986,382 B2 | 3/2015 | Bentley et al. |
| 9,020,789 B2 | 4/2015 | Butson et al. |
| 9,026,317 B2 | 5/2015 | Furukawa et al. |
| 9,039,740 B2 | 5/2015 | Wales et al. |
| 9,050,470 B2 | 6/2015 | Carlton et al. |
| 9,061,138 B2 | 6/2015 | Pianca |
| 9,072,905 B2 | 7/2015 | Kokones et al. |
| 9,081,488 B2 | 7/2015 | Soederstroem |
| 9,084,896 B2 | 7/2015 | Kokones et al. |
| 9,135,400 B2 | 9/2015 | Mcintyre et al. |
| 9,149,630 B2 | 10/2015 | Howard et al. |
| 9,162,056 B2 | 10/2015 | Pianca |
| 9,220,889 B2 | 12/2015 | Carlton et al. |
| 9,227,074 B2 | 1/2016 | Carcieri et al. |
| 9,235,685 B2 | 1/2016 | Mcintyre et al. |
| 9,248,272 B2 | 2/2016 | Romero |
| 9,248,296 B2 | 2/2016 | Carcieri et al. |
| 9,254,387 B2 | 2/2016 | Blum et al. |
| 9,272,153 B2 | 3/2016 | Blum et al. |
| 9,289,596 B2 | 3/2016 | Even |
| 9,289,600 B2 | 3/2016 | Govea et al. |
| 9,302,110 B2 | 4/2016 | Kokones et al. |
| 9,308,372 B2 | 4/2016 | Sparks et al. |
| 9,310,985 B2 | 4/2016 | Blum et al. |
| 9,327,111 B2 | 5/2016 | Pianca et al. |
| 9,358,398 B2 | 6/2016 | Moffitt et al. |
| 9,364,665 B2 | 6/2016 | Bokil et al. |
| 9,381,348 B2 | 7/2016 | Romero et al. |
| 9,387,325 B1 | 7/2016 | Min et al. |
| 9,415,154 B2 | 8/2016 | Leven |
| 9,474,903 B2 | 10/2016 | Chen et al. |
| 9,492,655 B2 | 11/2016 | Pianca et al. |
| 9,498,620 B2 | 11/2016 | Romero et al. |
| 9,526,902 B2 | 12/2016 | Blum et al. |
| 9,533,141 B2 | 1/2017 | Black et al. |
| 9,566,596 B2 | 2/2017 | Kim et al. |
| 9,572,982 B2 | 2/2017 | Burnes et al. |
| 9,586,053 B2 | 3/2017 | Moffitt et al. |
| 9,592,389 B2 | 3/2017 | Moffitt |
| 9,610,435 B2 | 4/2017 | Schleicher et al. |
| 9,636,498 B2 | 5/2017 | Leven |
| 9,649,489 B2 | 5/2017 | Wechter et al. |
| 9,669,210 B2 | 6/2017 | Barker et al. |
| 9,713,720 B2 | 7/2017 | Zhu |
| 9,775,988 B2 | 10/2017 | Govea et al. |
| 9,792,412 B2 | 10/2017 | Moffitt et al. |

(56)  References Cited

U.S. PATENT DOCUMENTS

| | | | |
|---|---|---|---|
| 9,821,167 | B2 | 11/2017 | Carcieri et al. |
| 9,887,470 | B2 | 2/2018 | Nguyen-Stella et al. |
| 9,925,382 | B2 | 3/2018 | Carlton et al. |
| 9,959,940 | B2 | 5/2018 | Moffitt et al. |
| 9,974,959 | B2 | 5/2018 | Moffitt et al. |
| 9,987,482 | B2 | 6/2018 | Nageri et al. |
| 10,067,659 | B2 | 9/2018 | Bokil |
| 10,071,242 | B2 | 9/2018 | Leven |
| 10,071,249 | B2 | 9/2018 | Zottola |
| 10,086,202 | B2 | 10/2018 | Seim et al. |
| 10,086,205 | B2 | 10/2018 | Grill et al. |
| 10,213,148 | B2 | 2/2019 | Min et al. |
| 10,226,616 | B2 | 3/2019 | Barker |
| 10,265,528 | B2 | 4/2019 | Carcieri et al. |
| 10,265,531 | B2 | 4/2019 | Bokil |
| 10,286,205 | B2 | 5/2019 | Steinke et al. |
| 10,300,282 | B2 | 5/2019 | Torgerson et al. |
| 10,335,607 | B2 | 7/2019 | Orinski |
| 10,357,657 | B2 | 7/2019 | Moffitt et al. |
| 10,369,364 | B2 | 8/2019 | Moffitt et al. |
| 10,406,353 | B2 | 9/2019 | Wechter |
| 10,485,969 | B2 | 11/2019 | Govea et al. |
| 10,493,269 | B2 | 12/2019 | Stoffregen et al. |
| 10,525,257 | B2 | 1/2020 | Govea et al. |
| 10,525,266 | B2 | 1/2020 | Moffitt et al. |
| 10,603,498 | B2 | 3/2020 | Blum et al. |
| 10,625,072 | B2 | 4/2020 | Serrano Carmona |
| 10,631,937 | B2 | 4/2020 | Tyulmankov et al. |
| 10,639,488 | B2 | 5/2020 | Kalgren et al. |
| 10,653,330 | B2 | 5/2020 | Angle et al. |
| 10,675,468 | B2 | 6/2020 | Torgerson |
| 10,709,886 | B2 | 7/2020 | Nagaoka et al. |
| 10,709,888 | B2 | 7/2020 | Pianca |
| 10,716,505 | B2 | 7/2020 | Blum et al. |
| 10,780,282 | B2 | 9/2020 | Mustakos et al. |
| 10,814,127 | B2 | 10/2020 | Nageri et al. |
| 10,814,140 | B2 | 10/2020 | Zhang et al. |
| 10,835,739 | B2 | 11/2020 | Sandhu |
| 10,850,101 | B2 | 12/2020 | Zhang et al. |
| 10,857,351 | B2 | 12/2020 | Wang et al. |
| 10,960,203 | B2 | 3/2021 | Tyler et al. |
| 11,020,052 | B2 | 6/2021 | Zuckerman-Stark et al. |
| 11,285,329 | B2 | 3/2022 | Carcieri et al. |
| 11,298,550 | B2 | 4/2022 | Howard et al. |
| 11,357,986 | B2 | 6/2022 | Steinke et al. |
| 11,517,755 | B2 | 12/2022 | Zhang et al. |
| 11,529,510 | B2 | 12/2022 | Leven |
| 11,707,622 | B2 | 7/2023 | Paz et al. |
| 11,745,010 | B2 | 9/2023 | Donega et al. |
| 2001/0031071 | A1 | 10/2001 | Nichols et al. |
| 2002/0032375 | A1 | 3/2002 | Bauch et al. |
| 2002/0062143 | A1 | 5/2002 | Baudino et al. |
| 2002/0087201 | A1 | 7/2002 | Firlik et al. |
| 2002/0099295 | A1 | 7/2002 | Gil et al. |
| 2002/0115603 | A1 | 8/2002 | Whitehouse |
| 2002/0116030 | A1 | 8/2002 | Rezei |
| 2002/0123780 | A1 | 9/2002 | Grill et al. |
| 2002/0128694 | A1 | 9/2002 | Holsheimer |
| 2002/0151939 | A1 | 10/2002 | Rezai |
| 2002/0183607 | A1 | 12/2002 | Bauch et al. |
| 2002/0183740 | A1 | 12/2002 | Edwards et al. |
| 2002/0183817 | A1 | 12/2002 | Van Venrooij et al. |
| 2003/0097159 | A1 | 5/2003 | Schiff et al. |
| 2003/0149450 | A1 | 8/2003 | Mayberg |
| 2003/0171791 | A1 | 9/2003 | KenKnight et al. |
| 2003/0212439 | A1 | 11/2003 | Schuler et al. |
| 2004/0034394 | A1 | 2/2004 | Woods et al. |
| 2004/0044279 | A1 | 3/2004 | Lewin et al. |
| 2004/0044378 | A1 | 3/2004 | Holsheimer |
| 2004/0044379 | A1 | 3/2004 | Holsheimer |
| 2004/0054297 | A1 | 3/2004 | Wingeier et al. |
| 2004/0059395 | A1 | 3/2004 | North et al. |
| 2004/0106916 | A1 | 6/2004 | Quaid et al. |
| 2004/0133248 | A1 | 7/2004 | Frei et al. |
| 2004/0152957 | A1 | 8/2004 | Stivoric et al. |
| 2004/0181262 | A1 | 9/2004 | Bauhahn |
| 2004/0186532 | A1 | 9/2004 | Tadlock |
| 2004/0193231 | A1 | 9/2004 | David et al. |
| 2004/0199216 | A1 | 10/2004 | Lee et al. |
| 2004/0267330 | A1 | 12/2004 | Lee et al. |
| 2005/0021090 | A1 | 1/2005 | Schuler et al. |
| 2005/0033380 | A1 | 2/2005 | Tanner et al. |
| 2005/0049649 | A1 | 3/2005 | Uders et al. |
| 2005/0060001 | A1 | 3/2005 | Singhal et al. |
| 2005/0060009 | A1 | 3/2005 | Goetz |
| 2005/0070781 | A1 | 3/2005 | Dawant et al. |
| 2005/0075689 | A1 | 4/2005 | Toy et al. |
| 2005/0085714 | A1 | 4/2005 | Foley et al. |
| 2005/0113885 | A1 | 5/2005 | Haubrich et al. |
| 2005/0165294 | A1 | 7/2005 | Weiss |
| 2005/0171587 | A1 | 8/2005 | Daglow et al. |
| 2005/0228250 | A1 | 10/2005 | Bitter et al. |
| 2005/0251061 | A1 | 11/2005 | Schuler et al. |
| 2005/0261061 | A1 | 11/2005 | Nguyen et al. |
| 2005/0261601 | A1 | 11/2005 | Schuler et al. |
| 2005/0261747 | A1 | 11/2005 | Schuler et al. |
| 2005/0267347 | A1 | 12/2005 | Oster |
| 2005/0288732 | A1 | 12/2005 | Schuler et al. |
| 2006/0004422 | A1 | 1/2006 | De Ridder |
| 2006/0017749 | A1 | 1/2006 | McIntyre et al. |
| 2006/0020292 | A1 | 1/2006 | Goetz et al. |
| 2006/0069415 | A1 | 3/2006 | Cameron et al. |
| 2006/0094951 | A1 | 5/2006 | Dean et al. |
| 2006/0095088 | A1 | 5/2006 | De Riddler |
| 2006/0155340 | A1 | 7/2006 | Schuler et al. |
| 2006/0173496 | A1 | 8/2006 | Lombardi et al. |
| 2006/0206169 | A1 | 9/2006 | Schuler |
| 2006/0218007 | A1 | 9/2006 | Bjorner et al. |
| 2006/0224189 | A1 | 10/2006 | Schuler et al. |
| 2006/0235472 | A1 | 10/2006 | Goetz et al. |
| 2006/0259079 | A1 | 11/2006 | King |
| 2006/0259099 | A1 | 11/2006 | Goetz et al. |
| 2007/0000372 | A1 | 1/2007 | Rezai et al. |
| 2007/0017749 | A1 | 1/2007 | Dold et al. |
| 2007/0027499 | A1 | 2/2007 | Maschino et al. |
| 2007/0027514 | A1 | 2/2007 | Gerber |
| 2007/0043268 | A1 | 2/2007 | Russell |
| 2007/0049817 | A1 | 3/2007 | Preiss et al. |
| 2007/0067003 | A1 | 3/2007 | Sanchez et al. |
| 2007/0078498 | A1 | 4/2007 | Rezai et al. |
| 2007/0083104 | A1 | 4/2007 | Butson et al. |
| 2007/0123953 | A1 | 5/2007 | Lee et al. |
| 2007/0129769 | A1 | 6/2007 | Bourget et al. |
| 2007/0135855 | A1 | 6/2007 | Foshee et al. |
| 2007/0150026 | A1 | 6/2007 | Bourget et al. |
| 2007/0150036 | A1 | 6/2007 | Anderson |
| 2007/0156186 | A1 | 7/2007 | Lee et al. |
| 2007/0162086 | A1 | 7/2007 | DiLorenzo |
| 2007/0162235 | A1 | 7/2007 | Zhan et al. |
| 2007/0168004 | A1 | 7/2007 | Walter |
| 2007/0168007 | A1 | 7/2007 | Kuzma et al. |
| 2007/0179557 | A1 | 8/2007 | Maschino et al. |
| 2007/0185544 | A1 | 8/2007 | Dawant et al. |
| 2007/0191887 | A1 | 8/2007 | Schuler et al. |
| 2007/0191912 | A1 | 8/2007 | Ficher et al. |
| 2007/0197891 | A1 | 8/2007 | Shachar et al. |
| 2007/0203450 | A1 | 8/2007 | Berry |
| 2007/0203532 | A1 | 8/2007 | Tass et al. |
| 2007/0203537 | A1 | 8/2007 | Goetz et al. |
| 2007/0203538 | A1 | 8/2007 | Stone et al. |
| 2007/0203539 | A1 | 8/2007 | Stone et al. |
| 2007/0203540 | A1 | 8/2007 | Goetz et al. |
| 2007/0203541 | A1 | 8/2007 | Goetz et al. |
| 2007/0203543 | A1 | 8/2007 | Stone et al. |
| 2007/0203544 | A1 | 8/2007 | Goetz et al. |
| 2007/0203545 | A1 | 8/2007 | Stone et al. |
| 2007/0203546 | A1 | 8/2007 | Stone et al. |
| 2007/0213789 | A1 | 9/2007 | Nolan et al. |
| 2007/0213790 | A1 | 9/2007 | Nolan et al. |
| 2007/0244519 | A1 | 10/2007 | Keacher et al. |
| 2007/0245318 | A1 | 10/2007 | Goetz et al. |
| 2007/0255321 | A1 | 11/2007 | Gerber et al. |
| 2007/0255322 | A1 | 11/2007 | Gerber et al. |
| 2007/0260283 | A1 | 11/2007 | Li |

(56)　　　　　References Cited

U.S. PATENT DOCUMENTS

| | | |
|---|---|---|
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0046037 A1 | 2/2008 | Haubrich et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0091248 A1 | 4/2008 | Libbus et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215101 A1 | 9/2008 | Rezai et al. |
| 2008/0215118 A1 | 9/2008 | Goetz et al. |
| 2008/0227139 A1 | 9/2008 | Deisseroth et al. |
| 2008/0238749 A1 | 10/2008 | Comdorf |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054947 A1 | 2/2009 | Bourn et al. |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0163975 A1 | 6/2009 | Gerber et al. |
| 2009/0187222 A1 | 7/2009 | Barker |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0228073 A1 | 9/2009 | Scholten |
| 2009/0242399 A1 | 10/2009 | Kamath et al. |
| 2009/0270949 A1 | 10/2009 | Kalpin et al. |
| 2009/0276008 A1 | 11/2009 | Lee et al. |
| 2009/0276021 A1 | 11/2009 | Meadows et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010387 A1 | 1/2010 | Skelton et al. |
| 2010/0010432 A1 | 1/2010 | Skelton |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0057161 A1 | 3/2010 | Machado et al. |
| 2010/0064249 A1 | 3/2010 | Groetken |
| 2010/0076535 A1 | 3/2010 | Pianca et al. |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0152807 A1 | 6/2010 | Grill et al. |
| 2010/0179562 A1 | 7/2010 | Linker et al. |
| 2010/0211135 A1 | 8/2010 | Caparso et al. |
| 2010/0268298 A1 | 10/2010 | Moffitt |
| 2010/0324410 A1 | 12/2010 | Paek et al. |
| 2010/0331883 A1 | 12/2010 | Schmitz et al. |
| 2011/0004267 A1 | 1/2011 | Meadows |
| 2011/0005069 A1 | 1/2011 | Pianca |
| 2011/0040351 A1 | 2/2011 | Buston et al. |
| 2011/0054559 A1 | 3/2011 | Rosenberg et al. |
| 2011/0066407 A1 | 3/2011 | Butson et al. |
| 2011/0078900 A1 | 4/2011 | Pianca et al. |
| 2011/0093045 A1 | 4/2011 | Moffitt |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0137372 A1 | 6/2011 | Makous et al. |
| 2011/0160796 A1 | 6/2011 | Lane et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0224665 A1 | 9/2011 | Crosby et al. |
| 2011/0224680 A1 | 9/2011 | Barker |
| 2011/0238129 A1 | 9/2011 | Moffitt |
| 2011/0251583 A1 | 10/2011 | Miyazawa et al. |
| 2011/0270348 A1 | 11/2011 | Goetz |
| 2011/0306845 A1 | 12/2011 | Osorio |
| 2011/0306846 A1 | 12/2011 | Osorio |
| 2011/0307032 A1 | 12/2011 | Goetz et al. |
| 2011/0313485 A1 | 12/2011 | DeMulling et al. |
| 2011/0313500 A1 | 12/2011 | Barker et al. |
| 2012/0016378 A1 | 1/2012 | Pianca et al. |
| 2012/0027272 A1 | 2/2012 | Akinyemi et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0078106 A1 | 3/2012 | Dentinger et al. |
| 2012/0089205 A1 | 4/2012 | Boyden et al. |
| 2012/0101552 A1 | 4/2012 | Lazarewicz et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0239109 A1 | 9/2012 | Lee |
| 2012/0239115 A1 | 9/2012 | Lee |
| 2012/0265103 A1 | 10/2012 | Policker et al. |
| 2012/0265262 A1 | 10/2012 | Osorio |
| 2012/0265268 A1 | 10/2012 | Blum et al. |
| 2012/0271189 A1 | 10/2012 | Nelson et al. |
| 2012/0277833 A1 | 11/2012 | Gerber et al. |
| 2012/0302912 A1 | 11/2012 | Moffitt et al. |
| 2012/0303087 A1 | 11/2012 | Moffitt et al. |
| 2012/0303098 A1 | 11/2012 | Perryman |
| 2012/0314919 A1 | 12/2012 | Sparks et al. |
| 2012/0314924 A1 | 12/2012 | Carlton et al. |
| 2012/0316615 A1 | 12/2012 | Digiore et al. |
| 2012/0316619 A1 | 12/2012 | Goetz et al. |
| 2012/0330374 A1 | 12/2012 | Blum et al. |
| 2012/0330622 A1 | 12/2012 | Butson et al. |
| 2013/0035740 A1 | 2/2013 | Sharma et al. |
| 2013/0039550 A1 | 2/2013 | Blum et al. |
| 2013/0053926 A1 | 2/2013 | Hincapie Ordonez et al. |
| 2013/0060301 A1 | 3/2013 | Polefko et al. |

(56) References Cited

U.S. PATENT DOCUMENTS

| | | |
|---|---|---|
| 2013/0060305 A1 | 3/2013 | Bokil |
| 2013/0105071 A1 | 5/2013 | Digiore et al. |
| 2013/0116744 A1 | 5/2013 | Blum et al. |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2013/0150922 A1 | 6/2013 | Butson et al. |
| 2013/0197424 A1 | 8/2013 | Bedenbaugh |
| 2013/0197602 A1 | 8/2013 | Pianca et al. |
| 2013/0226261 A1 | 8/2013 | Sparks et al. |
| 2013/0245722 A1 | 9/2013 | Ternes et al. |
| 2013/0261684 A1 | 10/2013 | Howard |
| 2013/0289380 A1 | 10/2013 | Molnar et al. |
| 2013/0289660 A1 | 10/2013 | Molnar et al. |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039586 A1 | 2/2014 | Barker et al. |
| 2014/0039587 A1 | 2/2014 | Romero |
| 2014/0063017 A1 | 3/2014 | Kaula et al. |
| 2014/0066999 A1 | 3/2014 | Carcieri et al. |
| 2014/0067018 A1 | 3/2014 | Carcieri et al. |
| 2014/0067022 A1 | 3/2014 | Carcieri et al. |
| 2014/0074180 A1 | 3/2014 | Heldman et al. |
| 2014/0081366 A1 | 3/2014 | Bentley et al. |
| 2014/0107731 A1 | 4/2014 | Stone et al. |
| 2014/0122379 A1 | 5/2014 | Moffitt et al. |
| 2014/0200633 A1 | 7/2014 | Moffitt |
| 2014/0243926 A1 | 8/2014 | Carcieri |
| 2014/0276707 A1 | 9/2014 | Jaax |
| 2014/0276927 A1 | 9/2014 | Barker |
| 2014/0277282 A1 | 9/2014 | Jaax |
| 2014/0277284 A1 | 9/2014 | Chen et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0073431 A1 | 3/2015 | Barker |
| 2015/0073432 A1 | 3/2015 | Barker |
| 2015/0134031 A1 | 5/2015 | Moffitt et al. |
| 2015/0151113 A1 | 6/2015 | Govea et al. |
| 2015/0246231 A1 | 9/2015 | Martens et al. |
| 2015/0360039 A1 | 12/2015 | Lempka et al. |
| 2016/0001087 A1 | 1/2016 | Moffitt |
| 2016/0008632 A1 | 1/2016 | Wetmore et al. |
| 2016/0022995 A1 | 1/2016 | Kothandaraman et al. |
| 2016/0023008 A1 | 1/2016 | Kothandaraman |
| 2016/0030749 A1 | 2/2016 | Carcieri et al. |
| 2016/0030750 A1 | 2/2016 | Bokil et al. |
| 2016/0045748 A1 | 2/2016 | Astrom et al. |
| 2016/0082252 A1 | 3/2016 | Hershey et al. |
| 2016/0096025 A1 | 4/2016 | Moffitt et al. |
| 2016/0136429 A1 | 5/2016 | Massoumi et al. |
| 2016/0136443 A1 | 5/2016 | Kothandaraman et al. |
| 2016/0144186 A1 | 5/2016 | Kaemmerer et al. |
| 2016/0175594 A1 | 6/2016 | Min et al. |
| 2016/0206380 A1 | 7/2016 | Sparks et al. |
| 2016/0228692 A1 | 8/2016 | Steinke et al. |
| 2016/0256691 A1 | 9/2016 | Cecchi et al. |
| 2016/0256693 A1 | 9/2016 | Parramon |
| 2016/0317800 A1 | 11/2016 | Barker |
| 2016/0346557 A1 | 12/2016 | Bokil |
| 2016/0375248 A1 | 12/2016 | Carcieri et al. |
| 2016/0375258 A1 | 12/2016 | Steinke |
| 2017/0100593 A1 | 4/2017 | Zottola |
| 2017/0100601 A1 | 4/2017 | Xiao et al. |
| 2017/0106197 A1 | 4/2017 | Wechter et al. |
| 2017/0197086 A1 | 7/2017 | Howard et al. |
| 2017/0225007 A1 | 8/2017 | Orinski |
| 2017/0252570 A1 | 9/2017 | Serrano Carmona et al. |
| 2017/0259078 A1 | 9/2017 | Howard |
| 2017/0304610 A1 | 10/2017 | Huibregtse et al. |
| 2017/0304633 A1 | 10/2017 | Zhang |
| 2017/0333692 A1 | 11/2017 | Stoffregen et al. |
| 2017/0372039 A1 | 12/2017 | Mustakos et al. |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0104500 A1 | 4/2018 | Blum et al. |
| 2018/0110971 A1 | 4/2018 | Serrano Carmona |
| 2018/0133481 A1 | 5/2018 | Von Zitzewitz et al. |
| 2018/0185650 A1 | 7/2018 | Shah |
| 2018/0193655 A1 | 7/2018 | Zhang et al. |
| 2018/0214700 A1 | 8/2018 | Vansickle et al. |
| 2018/0264278 A1 | 9/2018 | Laghi |
| 2018/0272142 A1 | 9/2018 | Zhang et al. |
| 2018/0280698 A1 | 10/2018 | Steinke et al. |
| 2018/0296828 A1 | 10/2018 | Bradley et al. |
| 2018/0333173 A1 | 11/2018 | Wang |
| 2018/0333587 A1 | 11/2018 | Howard |
| 2018/0369589 A1 | 12/2018 | Schouenborg |
| 2018/0369606 A1 | 12/2018 | Zhang et al. |
| 2018/0369607 A1 | 12/2018 | Zhang et al. |
| 2019/0015660 A1 | 1/2019 | Zhang et al. |
| 2019/0105503 A1 | 4/2019 | Leven |
| 2019/0184171 A1 | 6/2019 | Mustakos et al. |
| 2019/0209834 A1 | 7/2019 | Zhang et al. |
| 2019/0209849 A1 | 7/2019 | Hershey et al. |
| 2019/0262609 A1 | 8/2019 | Brill et al. |
| 2019/0275331 A1 | 9/2019 | Zhu |
| 2019/0329047 A1 | 10/2019 | Moffitt et al. |
| 2019/0329049 A1 | 10/2019 | Carcieri et al. |
| 2020/0094047 A1 | 3/2020 | Govea et al. |
| 2020/0139127 A1 | 5/2020 | Zhang et al. |
| 2020/0155854 A1 | 5/2020 | Leven et al. |
| 2020/0155859 A1 | 5/2020 | Blum et al. |
| 2020/0171298 A1 | 6/2020 | Goetz et al. |
| 2020/0171310 A1 | 6/2020 | Walter et al. |
| 2020/0179600 A1 | 6/2020 | Zanos et al. |
| 2020/0179701 A1 | 6/2020 | Pronovici et al. |
| 2020/0215330 A1 | 7/2020 | Huertas Fernandez et al. |
| 2020/0222704 A1 | 7/2020 | Moffitt et al. |
| 2020/0269053 A1 | 8/2020 | Park |
| 2020/0353254 A1 | 11/2020 | OLaighin et al. |
| 2020/0376262 A1 | 12/2020 | Clark et al. |
| 2020/0376263 A1 | 12/2020 | Zhu |
| 2020/0398057 A1 | 12/2020 | Esteller et al. |
| 2021/0008388 A1 | 1/2021 | Vansickle et al. |
| 2021/0008389 A1 | 1/2021 | Featherstone et al. |
| 2021/0016111 A1 | 1/2021 | Vansickle et al. |
| 2021/0023374 A1 | 1/2021 | Block et al. |
| 2021/0052893 A1 | 2/2021 | Suri et al. |
| 2021/0113844 A1 | 4/2021 | Zhang et al. |
| 2021/0128920 A1 | 5/2021 | Grill et al. |
| 2021/0196956 A1 | 7/2021 | Juárez Paz |
| 2021/0196964 A1 | 7/2021 | Schnell et al. |
| 2021/0205613 A1 | 7/2021 | Bradley et al. |
| 2021/0268268 A1 | 9/2021 | Horn et al. |
| 2021/0275820 A1 | 9/2021 | Grill, Jr. et al. |
| 2021/0387002 A1 | 12/2021 | Bourget et al. |
| 2022/0007980 A1 | 1/2022 | Single |
| 2022/0008729 A1 | 1/2022 | Zhu |
| 2022/0040485 A1 | 2/2022 | Li et al. |
| 2022/0062640 A1 | 3/2022 | Raike et al. |
| 2022/0072329 A1 | 3/2022 | Howard |
| 2022/0111213 A1 | 4/2022 | Cassar et al. |
| 2022/0126100 A1 | 4/2022 | Jackson et al. |
| 2022/0226641 A1 | 7/2022 | Subramanian |
| 2022/0257950 A1 | 8/2022 | Moore et al. |
| 2022/0266026 A1 | 8/2022 | Case et al. |
| 2022/0296892 A1 | 9/2022 | Esteller et al. |
| 2022/0296893 A1 | 9/2022 | Steinke et al. |
| 2022/0339448 A1 | 10/2022 | Jayakumar et al. |
| 2022/0347479 A1 | 11/2022 | Esteller et al. |

(56) References Cited

U.S. PATENT DOCUMENTS

| | | | |
|---|---|---|---|
| 2022/0355114 | A1 | 11/2022 | Moore et al. |
| 2022/0355115 | A1 | 11/2022 | Moore et al. |
| 2022/0370793 | A1 | 11/2022 | Foster et al. |
| 2022/0370808 | A1 | 11/2022 | Esteller |
| 2022/0387785 | A1 | 12/2022 | Huynh et al. |
| 2022/0395690 | A1 | 12/2022 | Haddock et al. |
| 2023/0048571 | A1 | 2/2023 | Poltorak |
| 2023/0064552 | A1 | 3/2023 | Moffitt |
| 2023/0141183 | A1 | 5/2023 | Moore et al. |
| 2023/0181089 | A1 | 6/2023 | Zhang et al. |
| 2023/0181090 | A1 | 6/2023 | Juarez Paz |
| 2023/0181906 | A1 | 6/2023 | Moore et al. |
| 2023/0248977 | A1 | 8/2023 | Esteller et al. |
| 2023/0264025 | A1 | 8/2023 | Malekmohammadi et al. |
| 2023/0271015 | A1 | 8/2023 | Malekmohammadi et al. |
| 2023/0277849 | A1 | 9/2023 | Moffitt et al. |
| 2023/0277854 | A1 | 9/2023 | Gaviao Kilmar |
| 2024/0058611 | A1 | 2/2024 | Steinke et al. |
| 2024/0065620 | A1 | 2/2024 | Moore et al. |
| 2024/0157151 | A1 | 5/2024 | Juarez Paz |
| 2024/0198110 | A1 | 6/2024 | Moore |
| 2024/0316346 | A1 | 9/2024 | Shah et al. |
| 2024/0359015 | A1 | 10/2024 | Steinke et al. |
| 2025/0010079 | A1 | 1/2025 | Bokil |
| 2025/0050107 | A1 | 2/2025 | Moore et al. |
| 2025/0099749 | A1 | 3/2025 | Moffitt et al. |
| 2025/0249236 | A1 | 8/2025 | Nageri et al. |
| 2025/0249251 | A1 | 8/2025 | Gu et al. |

FOREIGN PATENT DOCUMENTS

| | | |
|---|---|---|
| EP | 1166819 | 1/2002 |
| EP | 1372780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | WO2009134476 A1 | 11/2009 |
| WO | 2010/109448 | 9/2010 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |
| WO | 2016/025913 | 2/2016 |
| WO | 2016081099 | 5/2016 |
| WO | 2016112398 | 7/2016 |

OTHER PUBLICATIONS

Obeso, J. A., et al., "Deep-brain stimulation of the subthalamic nucleus or the pars interna of the globus pallidus in Parkinson's disease.", N Engl J Med., 345{13I. The Deep-Brain Stimulation for Parkinson's Disease Study Group, (Sep. 27, 2001 ),956-63.

Butson et al.. "Current Steering to control the vol. of tissue activated during deep brain stimulation," vol. 1, No. 1, Dec. 3, 2007, pp. 7-15.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.

Phillips, M. D., et al., "Parkinson disease: pattern of functional MR imaging activation during deep brain stimulation of subthalamic nucleus—initial experience", Radiology 239(1). (Apr. 2006),209-16.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

Mcintyre, C. C., et al., "How does deep brain stimulation work? Present understanding and future questions.", J Clin Neurophysiol. 21 (1 ). (Jan.-Feb. 2004 ),40-50.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

Plaha, P. , et al., "Stimulation of the caudal zona incerta is superior to stimulation of the subthalamic nucleus in Improving contralateral parkinsonism.", Brain 129{Pt 7) (Jul. 2006), 1732-4 7.

Rattay, F, "Analysis of models for external stimulation of axons", IEEE Trans. Biomed. Eng. vol. 33 (1986),974-977.

Rattay, F., "Analysis of the electrical excitation of CNS neurons", IEEE Transactions on Biomedical Engineering 45(6). (Jun. 1998),766-772.

Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.

Rubinstein, J. T., et al., "Signal coding in cochlear implants: exploiting stochastic effects of electrical stimulation", Ann Otol Rhinol Laryngol Suppl.. 191, (Sep. 2003), 14-9.

Schwan, H.P., et al., "The conductivity of living tissues.", Ann NY Acad Sci., 65(6). (Aug. 1957),1007-13.

Taylor, R. S., et al., "Spinal cord stimulation for chronic back and leg pain and failed back surgery syndrome: a systematic review and analysis of prognostic factors", Spine 30(1 ). (Jan. 1, 2005), 152-60.

Siegel, Ralph M. et al., "Spatiotemporal dynamics of the functional architecture for gain fields in inferior parietal obule of behaving monkey," Cerebral Cortex, New York, NY, vol. 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

Geddes, L. A., et al., "The specific resistance of biological material-a compendium of data for the biomedical engineer and physiologist.", Med Biol Ena. 5(3). (May 1967),271-93.

Gimsa, J., et al., "Choosing electrodes for deep brain stimulation experiments-electrochemical considerations.", J Neurosci Methods, 142(2), (Mar. 30, 2005),251-65.

Vidailhet, M. , et al., "Bilateral deep-brain stimulation of the globus pallidus in primary generalized dystonia", N Engl J Med. 352(5) (Feb. 3, 2005),459-67.

Izad, Oliver, "Computationally Efficient Method in Predicating Axonal Excitation," Dissertation for Master Degree, Department of Biomedical Engineering, Case Western Reserve University, May 2009.

(56)        References Cited

OTHER PUBLICATIONS

Jaccard, Paul, "Elude comparative de la distribution florale dans une portion odes Aples et des Jura," Bulletin de la Societe Vaudoise des Sciences Naturelles (1901), 37:547-579.

Dice, Lee R., "Measures of the Amount of Ecologic Association Between Species," Ecology 26(3) (1945): 297-302. doi: 10.2307/1932409, http://jstor.org/stable/1932409.

Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.

Hubert, Lawrence et al., "Comparing partitions," Journal of Classification 2(1) (1985): 193-218, doi:10.1007/BF01908075.

Cover, T.M. et al., "Elements of information theory," (1991) John Wiley & Sons, New York, NY.

Meila, Marina, "Comparing Clusterings by the Variation of Information," Learning Theory and Kernel Machines (2003): 173-187.

Viola, P., et al., "Alignment by maximization of mutual information", International Journal of Com outer Vision 24(2). ( 1997), 137-154.

Butson et al. "StimExplorer: Deep Brain Stimulation Parameter Selection Software System," Acta Neurochirugica, Jan. 1, 2007, vol. 97, No. 2, pp. 569-574.

Butson et al. "Role of Electrode Design on the Volume of Tissue Activated During Deep Brain Stimulation," Journal of Neural Engineering, Mar. 1, 2006, vol. 3, No. 1, pp. 1-8.

Volkmann et al., Indroduction to the Programming of Deep Brain Stimulators, Movement Disorders, vol. 17, Suppl. 3, pp. S181-S187 (2002).

Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.

Schmidt et al. "Sketching and Composing Widgets for 3D Manipulation," Eurographics, Apr. 2008, vol. 27, No. 2, pp. 301-310.

Volkmann, J. , et al., "Basic algorithms for the programming of deep brain stimulation in Parkinson's disease", Mov Disord., 21 Suppl 14. (Jun. 2006),S284-9.

Walter, B. L., et al., "Surgical treatment for Parkinson's disease", Lancet Neural. 3(12). (Dec., 2004),719-28.

Wei, X. F., et al., "Current density distributions, field distributions and impedance analysis of segmented deep brain stimulation electrodes", J Neural Eng .. 2(4). (Dec. 2005), 139-47.

Zonenshayn, M. , et al., "Location of the active contact within the subthalamic nucleus (STN) in the treatment of diopathic Parkinson's disease.", Surg Neurol., 62(3) (Sep. 2004),216-25.

Da Silva et al (A primer on diffusion tensor imaging of anatomical substructures. Neurosurg Focus 15(1): p. 1-4, Article 4, 2003.).

Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.

Grill, W. M., "Stimulus waveforms for selective neural stimulation", IEEE Engineering in Medicine and Biology Magazine, 14(4), (Jul.-Aug. 1995), 375-385.

Miocinovic, S., et al., "Sensitivity of temporal excitation properties to the neuronal element activated by extracellular stimulation", J Neurosci Methods. 132(1). (Jan. 15, 2004), 91-9.

Hunka, K. et al., Nursing Time to Program and Assess Deep Brain Stimulators in Movement Disorder Patients, J. Neursci Nurs., 37: 204-10 (Aug. 2005).

Moss, J. , et al., "Electron microscopy of tissue adherent to explanted electrodes in dystonia and Parkinson's disease", Brain, 127{Pt 12). (Dec. 2004 ),2755-63.

Montgomery, E. B., et al., "Mechanisms of deep brain stimulation and future technical developments.", Neurol Res. 22(3). (Apr. 2000),259-66.

Merrill, D. R., et al., "Electrical stimulation of excitable tissue: design of efficacious and safe protocols", J Neurosci Methods. 141(2), (Feb. 15, 2005), 171-98.

Fisekovic et al., "New Controller for Functional Electrical Stimulation Systems", Med. Eng. Phys. 2001; 23:391-399.

Butson et al., "Tissue and Electrode Capacitance Reduce Neural Activation Volumes During Deep Brain Stimulation", Clinical Neurophysiology, 116:2490-2500, Oct. 2005.

Butson et al., "Sources and Effects of Electrode Impedance During Deep Brain Stimulation", Clinical Neurophysiology, 117:44 7-454, Dec. 2005.

D'Haese et al., "Computer-Aided Placement of Deep Brain Stimulators: From Planning to Intraoperative Guidance", IEEE Transaction on Medical Imaging, 24:1469-1478, Nov. 2005.

Gross et al., "Electrophysiological Mapping for the Implantation of Deep Brain Stimulators for Parkinson's Disease and Tremor", Movement Disorders, 21 :S259-S283, Jun. 2006.

Halpern et al., "Brain Shift During Deep Brain Stimulation Surgery for Parkinson's Disease", Stereotact Funct. Neurosurg., 86:37-43, published online Sep. 2007.

Herzog et al., "Most Effective Stimulation Site in Subthalamic Deep Brain Stimulation for Parkinson's Disease", Movement Disorders, 19:1050-1099, published on line Mar. 2004.

Jeon et al., A Feasibility Study of Optical Coherence Tomography for Guiding Deep Brain Probes, Journal of Neuroscience Methods, 154:96-101, Jun. 2006.

Khan et al., "Assessment of Brain Shift Related to Deep Brain Stimulation Surgery", Sterreotact Funct. Neurosurg., 36:44-53, published online Sep. 2007.

Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.

Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.

Machado et al., "Deep Brain Stimulation for Parkinson's Disease: Surgical Technique and Perioperative Management", Movement Disorders, 21 :S247-S258, Jun. 2006.

Maks et al., "Deep Brain Stimulation Activation vols. and Their Association with Neurophysiological Mapping and Therapeutic Outcomes", Downloaded from jnnp.bmj.com, pp. 1-21, published online Apr. 2008.

Moran et al., "Real-Time Refinment of Subthalamic Nucleous Targeting Using Bayesian Decision-Making on the Root Mean Square Measure", Movement Disorders, 21: 1425-1431, published online Jun. 2006.

Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.

Winkler et al., The First Evaluation of Brain Shift During Functional Neurosurgery by Deformation Field Analysis, J. Neural. Neurosurg. Psychiatry, 76:1161-1163, Aug. 2005.

Yelnik et al., "A Three-Dimensional, Histological and Deformable Atlas of the Human Basal J Ganglia. I. Atlas Construction Based on Immunohistochemical and MRI Data", NeuroImage, 34:618,-638, Jan. 2007.

Ward, H. E., et al., "Update on deep brain stimulation for neuropsychiatric disorders," Neurobiol Dis 38 (3) (2010), pp. 346-353.

Alberts et al. "Bilateral subthalamic stimulation impairs cognitive-motor performance in Parkinson's disease patients." Brain (2008), 131, 3348-3360, Abstract.

Butson, Christopher R., et al., "Sources and effects of electrode impedance during deep brain stimulation", Clinical Neurophysiology. vol. 117.(2006),447-454.

An, et al., "Prefrontal cortical projections to longitudinal columns in the midbrain periaqueductal gray in macaque monkeys," J Comp Neural 401 (4) (1998), pp. 455-479.

Bulson, C. R., et al., "Tissue and electrode capacitance reduce neural activation vols. during deep brain stimulation," Clinical Neurophysiology, vol. 116 (2005), pp. 2490-2500.

(56) References Cited

OTHER PUBLICATIONS

Carmichael, S. T., et al., "Connectional networks within the orbital and medial prefrontal cortex of macaque monkeys," J Comp Neural 371 (2) (1996), pp. 179-207.

Croxson, et al., "Quantitative investigation of connections of the prefrontal cortex in the human and macaque using probabilistic diffusion tractography," J Neurosci 25 (39) (2005), pp. 8854-8866.

Frankemolle, et al., "Reversing cognitive-motor impairments in Parkinson's disease patients using a computational modelling approach to deep brain stimulation programming," Brain 133 (2010), pp. 746-761.

Freedman, et al., "Subcortical projections of area 25 (subgenual cortex) of the macaque monkey," J Comp Neurol 421 (2) (2000), pp. 172-188.

Giacobbe, et al., "Treatment resistant depression as a failure of brain homeostatic mechanisms: implications for deep brain stimulation," Exp Neural 219 (1) (2009), pp. 44-52.

Goodman, et al., "Deep brain stimulation for intractable obsessive compulsive disorder: pilot study using a blinded, staggered-onset design," Biol Psychiatry 67 (6) (2010), pp. 535-542.

Greenberg, et al., "Deep brain stimulation of the ventral internal capsule/ventral striatum for obsessive-compulsive disorder: world-wide experience," Mol Psychiatry 15 (1) (2010), pp. 64-79.

Greenberg et al., "Three-year outcomes in deep brain stimulation for highly resistant obsessive-compulsive disorder," Neuropsychopharmacology 31 (11) (2006), pp. 2384-2393.

Gutman, et al., "A tractography analysis of two deep brain stimulation white matter targets for depression," Biol Psychiatry 65 (4) (2009), pp. 276-282.

Haber, et al., "Reward-related cortical inputs define a large striatal region in primates that interface with associative cortical connections, providing a substrate for incentive-based learning," J Neurosci 26 (32) (2006), pp. 8368-8376.

Haber, et al., "Cognitive and limbic circuits that are affected by deep brain stimulation," Front Biosci 14 (2009), pp. 1823-1834.

Hines, M. L., et al., "The NEURON simulation environment," Neural Comput., 9(6) (Aug. 15, 1997), pp. 1179-1209.

Hua, et al., "Tract probability maps in stereotaxic spaces: analyses of white matter anatomy and tract-specific quantification," Neuroimage 39 (1) (2008), pp. 336-347.

Johansen-Berg, et al., "Anatomical connectivity of the subgenual cingulate region targeted with deep brain stimulation for treatment-resistant depression," Cereb Cortex 18 (6) (2008), pp. 1374-1383.

Kopell, et al., "Deep brain stimulation for psychiatric disorders," J Clin Neurophysiol 21 (1) (2004), pp. 51-67.

Lozano, et al., "Subcallosal cingulate gyrus deep brain stimulation for treatment-resistant depression," Biol Psychiatry 64 (6) (2008), pp. 461-467.

Lujan, et al., "Tracking the mechanisms of deep brain stimulation for neuropsychiatric disorders," Front Biosci 13 (2008), pp. 5892-5904.

Lujan, J.L. et al., "Automated 3-Dimensional Brain Atlas Fitting to Microelectrode Recordings from Deep Brain Stimulation Surgeries," Stereotact. Fune !. Neurosurg. 87(2009), pp. 229-240.

Machado. et al., "Functional topography of the ventral striatum and anterior limb of the internal capsule determined by electrical stimulation of awake patients," Clin Neurophysiol 120 (11) (2009), pp. 1941-1948.

Malone, et al., "Deep brain stimulation of the ventral capsule/ventral striatum for treatment-resistant depression," Biol Psychiatry 65 (4) (2009), pp. 267-275.

Mayberg, H. S., et al., "Deep brain stimulation for treatment-resistant depression," Neuron, 45(5) (Mar. 3, 2005), pp. 651-660.

Mayberg, H. S., et al., "Limbic-cortical dysregulation: a proposed model of depression," J Neuropsychiatry Clin Neurosci. 9 (3) (1997), pp. 471-481.

McIntyre, C. C., et al., "Network perspectives on the mechanisms of deep brain stimulation," Neurobiol Dis 38 (3) (2010), pp. 329-337.

Miocinovic, S., et al., "Experimental and theoretical characterization of the voltage distribution generated by deep brain stimulation," Exp Neurol 216 (i) (2009), pp. 166-176.

Nuttin, et al., "Electrical stimulation in anterior limbs of internal capsules in patients with obsessive-compulsive disorder," Lancet 354 (9189) (1999), p. 1526.

Saxena, et al., "Cerebral glucose metabolism in obsessive-compulsive hoarding," Am J Psychiatry. 161 (6) (2004), pp. 1038-1048.

Viola, et al., "Importance-driven focus of attention," IEEE Trans Vis Comput Graph 12 (5) (2006), pp. 933-940.

Wakana, S., et al., "Reproducibility of quantitative tractography methods applied to cerebral white matter," Neuroimage 36 (3) (2007), pp. 630-644.

Mayr et al., "Basic Design and Construction of the Vienna FES Implants: Existing Solutions and Prospects for New Generations of Implants", Medical Engineering & Physics, 2001; 23:53-60.

Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.

Mcintyre, Cameron C., et al., "Electric field generated by deep brain stimulation of the subthalamic nucleus," Biomedical Engineering Society Annual Meeting, Nashville TN (Oct. 2003), 16 pages.

Mcintyre, Cameron C., et al., "Excitation of central nervous system neurons by nonuniform electric fields," Biophys. J., 76(2) (1999), pp. 878-888.

McNeal, DR., et al., "Analysis of a model for excitation of myelinated nerve," IEEE Trans Biomed Eng., vol. 23 (1976), pp. 329-337.

Micheli-Tzanakou, E. , et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.

Miocinovic, S., et al., "Computational analysis of subthalamic nucleus and lenticular fasciculus activation during therapeutic deep brain stimulation," J Neurophysiol., 96(3) (Sep. 2006), pp. 1569-1580.

Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.

Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.

Moffitt, MA., et al., "Prediction of myelinated nerve fiber stimulation thresholds: limitations of linear models," IEEE Transactions on Biomedical Engineering, 51 (2) (2003), pp. 229-236.

Moro, E, et al., "The impact on Parkinson's disease of electrical parameter settings in STN stimulation," Neurology, 59 (5) (Sep. 10, 2002), pp. 706-713.

Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.

Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.

O'Suilleabhain, PE., et al., "Tremor response to polarity, voltage, pulsewidth and frequency of thalamic stimulation," Neurology, 60(5) (Mar. 11, 2003), pp. 786-790.

Pierpaoli, C., et al., "Toward a quantitative assessment of diffusion anisotropy," Magn Reson Med., 36(6) (Dec. 1996), pp. 893-906.

Plonsey, R., et al., "Considerations of quasi-stationarity in electrophysiological systems, " Bull Math Biophys., 29(4) (Dec. 1967), pp. 657-664.

Ranck, J B., "Specific impedance of rabbit cerebral cortex," Exp. Neurol., vol. 7 (Feb. 1963), pp. 144-152.

Ranck, J B., et al., "The Specific impedance of the dorsal columns of the cat: an anisotropic medium," Exp. Neurol., 11 (Apr. 1965), pp. 451-463.

(56) References Cited

OTHER PUBLICATIONS

Ranck, J B., "Which elements are excited in electrical stimulation of mammalian central nervous system: a review," Brain Res., 98(3) (Nov. 21, 1975), pp. 417-440.

Rattay, F., et al., "A model of the electrically excited human cochlear neuron. I. Contribution of neural substructures to the generation and propagation of spikes," Hear Res., 153(1-2) (Mar. 2001), pp. 43-63.

Rattay, F., "A model of the electrically excited human cochlear neuron. II. Influence of the three-dimensional cochlear structure on neural excitability," Hear Res., 153(1-2) (Mar. 2001), pp. 64-79.

Rattay, F., "Arrival at Functional Electrostimulation by modelling of fiber excitation," Proceedings of the Ninth annual Conference of the IEEE Engineering in Medicine and Biology Society (1987), pp. 1459-1460.

Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.

Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.

Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.

Sances, A., et al., "In Electroanesthesia: Biomedical and Biophysical Studies," A Sances and SJ Larson, Eds., Academic Press, NY (1975), pp. 114-124.

SI. Jean, P., et al., "Automated atlas integration and interactive three-dimensional visualization tools for planning and guidance in functional neurosurgery," IEEE Transactions on Medical Imaging, 17(5) (1998), pp. 672-680.

Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.

Sterio, D., et al., "Neurophysiological refinement of subthalamic nucleus targeting," Neurosurgery, 50(1) (Jan. 2002), pp. 58-69.

Struijk, J. J., et al., "Excitation of dorsal root fibers in spinal cord stimulation: a theoretical study," IEEE Transactions on Biomedical Engineering, 40(7) (Jul. 1993), pp. 632-639.

Struijk, J J., et al., "Recruitment of dorsal col. fibers in spinal cord stimulation: influence of collateral branching," IEEE Transactions on Biomedical Engineering, 39(9) (Sep. 1992), pp. 903-912.

Tamma, F., et al., "Anatomo-clinical correlation of intraoperative stimulation-induced side effects during HF-DBS of the subthalamic nucleus," Neurol Sci., vol. 23 (Suppl 2) (2002), pp. 109-110.

Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.

Testerman, Roy L., "Coritical response to callosal stimulation: A model for determining safe and efficient stimulus parameters," Annals of Biomedical Engineering, 6(4) (1978), pp. 438-452.

Tuch, D.S., et al., "Conductivity mapping of biological tissue using diffusion MRI," Ann NY Acad Sci., 888 (Oct. 30, 1999), pp. 314-316.

Tuch, D.S., et al., "Conductivity tensor mapping of the human brain using diffusion tensor MRI," Proc Nall Acad Sci USA, 98(20) (Sep. 25, 2001), pp. 11697-11701.

Veraart, C., et al., "Selective control of muscle activation with a multipolar nerve cuff electrode," IEEE Transactions on Biomedical Engineering, 40(7) (Jul. 1993), pp. 640-653.

Vercueil, L., et al., "Deep brain stimulation in the treatment of severe dystonia," J. Neurol., 248(8) (Aug. 2001 ), pp. 695-700.

Vilalte, "Circuit Design of the Power-on-Reset," Apr. 2000, pp. 1-25.

Vitek, J. L., "Mechanisms of deep brain stimulation: excitation or inhibition," Mov. Disord., vol. 17 (Suppl. 3) (2002), pp. 69-72.

Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.

Nakana, S., et al., "Fiber tract-based atlas of human white matter anatomy," Radiology, 230(1) (Jan. 2004), pp. 77-87.

Alexander, DC., et al., "Spatial transformations of diffusion tensor magnetic resonance images," IEEE Transactions on Medical Imaging, 20 (11), (2001), pp. 1131-1139.

Wu, Y. R., et al., "Does Stimulation of the GPi control dyskinesia by activating inhibitory axons?," Mov. Disord., vol. 16 (2001), pp. 208-216.

Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.

Manni, John, et al., "Globus pallidus internus deep brain stimulation for dystonic conditions: a prospective audit," Mov. Disord., vol. 18 (2003), pp. 436-442.

Zonenshayn, M., et al., "Comparison of anatomic and neurophysiological methods for subthalamic nucleus targeting," Neurosurgery, 47(2) (Aug. 2000), pp. 282-294.

Voghell et al., "Programmable Current Source Dedicated to Implantable Microstimulators" ICM '98 Proceedings of the Tenth International Conference, pp. 67-70.

Butson, Christopher R., et al., "Patient-specific analysis of the volume of tissue activated during deep brain stimulation", NeuroImage. vol. 34. (2007),661-670.

Adler, DE., et al., "The tentorial notch: anatomical variation, morphometric analysis, and classification in 100 human autopsy cases," J. Neurosurg., 96(6), (Jun. 2002), pp. 1103-1112.

Jones et al., "An Advanced Demultiplexing System for Physiological Stimulation", IEEE Transactions on Biomedical Engineering, vol. 44 No. Dec. 12, 1997, pp. 1210-1220.

International Search Report and Written Opinion for PCT Application No. PCT/US2022/051951 mailed Mar. 30, 2023.

Zhang, Y., et al., "Atlas-guided tract reconstruction for automated and comprehensive examination of the white matter anatomy," Neuroimage 52(4) (2010), pp. 1289-1301.

""BioPSE" The Biomedical Problem Solving Environment", htt12:// www.sci.utah.edu/cibc/software/index.html, MCRR Center for Integrative Biomedical Computing,(2004).

Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003),1-13.

Carnevale, N.T. et al., "The Neuron Book," Cambridge, UK: Cambridge University Press (2006), 480 pages.

Chaturvedi: "Development of Accurate Computational Models for Patient-Specific Deep Brain Stimulation," Electronic Thesis or Dissertation, Jan. 2012, 162 pages.

Chaturvedi, A. et al.: "Patient-specific models of deep brain stimulation: Influence of field model complexity on neural activation predictions." Brain Stimulation, Elsevier, Amsterdam, NL, vol. 3, No. Apr. 2, 2010, pp. 65-77.

Frankemolle, et al., "Reversing cognitive-motor impairments in Parkinson's disease patients using a computational modeling approach to deep brain stimulation programming," Brian 133 (2010), pp. 746-761.

Mcintyre, C.C., et al., "Modeling the excitablitity of mammalian nerve fibers: influence of afterpotentials on the recovery cycle," J Neurophysiol, 87(2) (Feb. 2002), pp. 995-1006.

Peterson, et al., "Predicting myelinated axon activation using spatial characteristics of the extracellular field," Journal of Neural Engineering, 8 (2011), 12 pages.

Warman, et al., "Modeling the Effects of Electric Fields on nerver Fibers; Dermination of Excitation Thresholds," IEEE Transactions on Biomedical Engineering, vol. 39, No. 12 (Dec. 1992), pp. 1244-1254.

(56)         References Cited

OTHER PUBLICATIONS

Wesselink, et al., "Analysis of Current Density and Related Parameters in Spinal Cord Stimulation," IEEE Transactions on Rehabilitation Engineering, vol. 6, No. Jun. 2, 1998, pp. 200-207.

Andrews, R. J., "Neuroprotection trek-the next generation: neuromodulation II. Applications—epilepsy, nerve regeneration, neurotrophins.", Ann NY Acad Sci. 993 (May 2003), 14-24.

Astrom, M. , et al., "The effect of cystic cavities on deep brain stimulation in the basal ganglia: a simulation-based study", J Neural Eng., 3(2), (Jun. 2006).132-8.

Bazin et al., "Free Software Tools for Atlas-based Volumetric Neuroimage Analysis", Proc. SPIE 5747, Medical Imaging 2005: Image Processing, 1824 May 5, 2005.

Back, C. , et al., "Postoperative Monitoring of the Electrical Properties of Tissue and Electrodes in Deep Brain Stimulation", Neuromodulation, 6(4), (Oct. 2003 ),248-253.

Baker, K. B., et al., "Evaluation of specific absorption rate as a dosimeter of MRI-related implant heating", J Magn Reson Imaging., 20(2), (Aug. 2004),315-20.

Brown, J. "Motor Cortex Stimulation," Neurosurgical Focus ( Sep. 15, 2001) 11(3):E5.

Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.

Cesselin, F. "Opioid and anti-opioid peptides," Fundamental and Clinical Pharmacology (1995) 9(5): 409-33 (Abstract only).

Rezai et al., "Deep Brain Stimulation for Chronic Pain" Surgical Management of Pain, Chapter 44 pp. 565-576 (2002).

Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.

Bedard, C. , et al., "Modeling extracellular field potentials and the frequency-filtering properties of extracellular space", Biophys J .. 86(3). (Mar. 2004),1829-42.

Benabid, A. L., et al., "Future prospects of brain stimulation", Neurol Res.,22(3), (Apr. 2000),237-46.

Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.

Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.

Mcintyre, Cameron C., et al., "Cellular effects of deep brain stimulation: model-based analysis of activation and Inhibition," J Neurophysiol, 91(4) (Apr. 2004), pp. 1457-1469.

Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.

Butson, Christopher et al., "Predicting the Effects of Deep Brain Stimulation with Diffusion Tensor Based Electric Field Models" Jan. 1, 2001, Medical Image Computing and Computer-Assisted Intervention—Mic CAI 2006 Lecture Notes in Computer Science; LNCS, Springer, Berlin, DE.

Butson, C. R., et al., "Deep brainstimulation interactive visualization system", Society for Neuroscience vol. 898.7 (2005).

Hodaie, M., et al., "Chronic anterior thalamus stimulation for intractable epilepsy," Epilepsia, 43(6) (Jun. 2002), pp. 603-608.

Hoekema, R., et al., "Multigrid solution of the potential field in modeling electrical nerve stimulation," Comput Biomed Res., 31(5) (Oct. 1998), pp. 348-362.

Holsheimer, J., et al., "Identification of the target neuronal elements in electrical deep brain stimulation," Eur J Neurosci., 12(12) (Dec. 2000), pp. 4573-4577.

Jezernik, S., et al., "Neural network classification of nerve activity recorded in a mixed nerve," Neurol Res., 23(5) (Jul. 2001), pp. 429-434.

Jones, DK., et al., "Optimal strategies for measuring diffusion in anisotropic systems by magnetic resonance imaging," Magn. Reson. Med., 42(3) (Sep. 1999), pp. 515-525.

Krack, P., et al., "Postoperative management of subthalamic nucleus stimulation for Parkinson's disease," Mov. Disord., vol. 17(suppl 3) (2002), pp. 188-197.

Le Bihan, D., et al., "Diffusion tensor imaging: concepts and applications," J Magn Reson Imaging, 13(4) (Apr. 2001), pp. 534-546.

Lee, D. C., et al., "Extracellular electrical stimulation of central neurons: quantitative studies," In: Handbook of neuroprosthetic methods, WE Finn and PG Lopresti (eds) CRC Press (2003), pp. 95-125.

Levy, AL., et al., "An Internet-connected, patient-specific, deformable brain atlas integrated into a surgical navigation system," J Digit Imaging, 10(3 Suppl 1) (Aug. 1997), pp. 231-237.

Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.

Mcintyre, C. C., et al., "Extracellular stimulation of central neurons: influence of stimulus waveform and frequency on neuronal output," J. Neurophysiol., 88(4), (Oct. 2002), pp. 1592-1604.

Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.

Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.

Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.

Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.

Mcintyre, Cameron C., et al., "Modeling the excitability of mammalian nerve fibers: influence of aflerpotentials on the recovery cycle," J Neurophysiol, 87(2) (Feb. 2002), pp. 995-1006.

Mcintyre, Cameron C., et al., "Selective microstimulation of central nervous system neurons," Annals of biomedical engineering, 28(3) (Mar. 2000), pp. 219-233.

Mcintyre, C. C., et al., "Sensitivity analysis of a model of mammalian neural membrane," Biol Cybern., 79(1) (Jul. 1998), pp. 29-37.

Mcintyre, Cameron C., et al., "Uncovering the mechanism(s) of action of deep brain stimulation: activation, inhibition, or both," Clin Neurophysiol, 115(6) (Jun. 2004), pp. 1239-1248.

Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.

Mouine et al. "Multi-Strategy and Multi-Algorithm Cochlear Prostheses", Biomed. Sci. Instrument, 2000; 36:233-238.

Alo, K. M., et al., "New trends in neuromodulation for the management of neuropathic pain," Neurosurgery, 50(4), (Apr. 2002), pp. 690-703, discussion pp. 703-704.

Ashby, P., et al., "Neurophysiological effects of stimulation through electrodes in the human subthalamic nucleus," Brain, 122 (PI 10), (Oct. 1999), pp. 1919-1931.

Baker, K. B., et al., "Subthalamic nucleus deep brain stimulus evoked potentials: Physiological and therapeutic Implications," Movement Disorders, 17(5), (Sep./Oct. 2002), pp. 969-983.

(56)            References Cited

OTHER PUBLICATIONS

Bammer, R, et al., "Diffusion tensor imaging using single-shot SENSE-EPI", Magn Reson Med., 48(1 ), (Jul. 2002), pp. 128-136.

Basser, P.J., et al., "MR diffusion tensor spectroscopy and imaging," Biophys J., 66(1 ), (Jan. 1994), pp. 259-267.

Basser, P J., et al., "New currents in electrical stimulation of excitable tissues," Annu Rev Biomed Eng., 2, (2000), pp. 377-397.

Benabid, AL., et al., "Chronic electrical stimulation of the ventralis intermedius nucleus of the thalamus as a treatment of movement disorders," J. Neurosurg., 84(2), (Feb. 1996), pp. 203-214.

Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.

Benabid, A L., et al., "Long-term suppression of tremor by chronic stimulation of the ventral intermediate thalamic nucleus," Lancet, 337 (8738), (Feb. 16, 1991 ), pp. 403-406.

Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.

Christensen, Gary E., et al., "Volumetric transformation of brain anatomy," IEEE Transactions on Medical Imaging, 16 (6), (Dec. 1997), pp. 864-877.

Cooper, S , et al., "Differential effects of thalamic stimulation parameters on tremor and paresthesias in essential tremor," Movement Disorders, 17(Supp. 5), (2002), p. S193.

Coubes, P, et al., "Treatment of DYT1-generalised dystonia by stimulation of the internal globus pallidus," Lancet, 355 (9222), (Jun. 24, 2000), pp. 2220-2221.

Dasilva, A.F. M., et al., "A Primer Diffusion Tensor Imaging of Anatomical Substructures," Neurosurg. Focus; 15(1) (Jul. 2003), pp. 1-4.

Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.

Finnis, K. W., et al., "3-D functional atalas of subcortical structures for image guided stereotactic neurosurgery," Neuroimage, vol. 9, No. 6, Iss. 2 (1999), p. S206.

Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.

Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes In Computer Science; vol. 1935 (2000), pp. 1-8.

Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.

Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes In Computer Science; vol. 2489 (2002), pp. 69-76.

Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.

Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.

Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.

Gabriels, LA., et al., "Long-term electrical capsular stimulation in patients with obsessive-compulsive disorder," Neurosurgery, 52(6) (Jun. 2003), pp. 1263-1276.

Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.

Goodall, E. V., et al., "Position-selective activation of peripheral nerve fibers with a cuff electrode," IEEE Transactions on Biomedical Engineering, 43(8) (Aug. 1996), pp. 851-856.

Goodall, E. V., "Simulation of activation and propagation delay during tripolar neural stimulation," Proceedings of the 15th Annual International Conference of the IEEE Engineering in Medicine and Biology Society (1993), pp. 1203-1204.

Grill, WM., "Modeling the effects of electric fields on nerve fibers: influence of tissue electrical properties," IEEE Transactions on Biomedical Engineering, 46(8) (1999), pp. 918-928.

Grill, W. M., et al., "Neural and connective tissue response to long-term implantation of multiple contact nerve cuff electrodes," J Biomed Mater Res., 50(2) (May 2000), pp. 215-226.

Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.

Grill, W. M., et al., "Non-invasive measurement of the input-output properties of peripheral nerve stimulating electrodes," Journal of Neuroscience Methods, 65(1) (Mar. 1996), pp. 43-50.

Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.

Grill, W. M., "Spatially selective activation of peripheral nerve for neuroprosthetic applications," Ph.D. Case Western Reserve University, (1995), pp. 245 pages.

Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.

Grill, W. M., "Stimulus waveforms for selective neural stimulation," IEEE Engineering in Medicine and Biology Magazine, 14(4) (Jul.-Aug. 1995), pp. 375-385.

Grill, W. M., et al., "Temporal stability of nerve cuff electrode recruitment properties," IEEE 17th Annual Conference Engineering in Medicine and Biology Society, vol. 2 (1995), pp. 1089-1090.

Gross, RE., et al., "Advances in neurostimulation for movement disorders," Neurol Res., 22(3) (Apr. 2000), pp. 247-258.

Guridi et al., "The subthalamic nucleus, hemiballismus and Parkinson's disease: reappraisal of a neurological dogma," Brain, vol. 124, 2001, pp. 5-19.

Haberler, C, et al., "No. tissue damage by chronic deep brain stimulation in Parkinson's disease," Ann Neurol., 48(3) (Sep. 2000), pp. 372-376.

Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.

Hanekom, "Modelling encapsulation tissue around cochlear implant electrodes," Med. Biol. Eng. Comput. vol. 43 (2005), pp. 47-55.

Haueisen, J , et al., "The influence of brain tissue anisotropy on human EEG and MEG," Neuroimage, 15(1) (Jan. 2002), pp. 159-166.

D'Haese et al. Medical Image Computing and Computer-Assisted Intervention—MICCAI 2005 Lecture Notes in Computer Science, 2005, vol. 3750, 2005, 427-434.

(56)　　　　　References Cited

OTHER PUBLICATIONS

Rohde et al. IEEE Transactions on Medical Imaging, vol. 22 No. 11, 2003 p. 1470-1479.

Dawant et al., Biomedical Image Registration. Lecture Notes in Computer Science, 2003, vol. 2717, 2003, 142-150.

Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.

Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.

Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.

Andrade-Souza, "Comparison of Three Methods of Targeting the Subthalamic Nucleus for Chronic Stimulation in Parkinson's Disease", Neurosurgery, 56:360-368, Apr. 2005.

Anheim et al., "Improvement in Parkinson Disease by Subthalamic Nucleus Stimulation Based on Electrode Placement", Arch Neural., 65:612-616, May 2008.

Mitra PP, Pesaran B. Analysis of dynamic brain imaging data. Biophys J. Feb. 1999;76(2):691-708. doi: 10.1016/S0006-3495(99)77236-X. PMID: 9929474; PMCID: PMC1300074.

Hammer N, Glätzner J, Feja C, Kühne C, Meixensberger J, et al. (2015) Human Vagus Nerve Branching in the Cervical Region. Plos One 10(2): e0118006. Published: Feb. 13, 2015. https://doi.org/10.1371/journal.pone.0118006.

Trost M, Su S, Su P, Yen RF, Tseng HM, Barnes A, Ma Y, Eidelberg D. Network modulation by the subthalamic nucleus in the treatment of Parkinson's disease. Neuroimage. May 15, 2006;31(1):301-7. doi: 10.1016/j.neuroimage.2005.12.024. Epub Feb. 8, 2006.

Mcintyre, Cameron , et al., "Finite element analysis of the current-density and electric field generated by metal microelectrodes", Ann Biomed Eng . 29(3), (2001 ),227-235.

Foster, K. R., et al., "Dielectric properties of tissues and biological materials: a critical review.", Grit Rev Biomed Ena. 17(1 ). {1989),25-104.

Limousin, P., et al., "Electrical stimulation of the subthalamic nucleus in advanced Parkinson's disease", N Engl J Med . . . 339(16), (Oct. 15, 1998), 1105-11.

Kitagawa, M., et al., "Two-year follow-up of chronic stimulation of the posterior subthalamic white matter for tremor-dominant Parkinson's disease.", Neurosurgery. 56(2). (Feb. 2005),281-9.

Johnson, M. D., et al., "Repeated voltage biasing improves unit recordings by reducing resistive tissue impedances", IEEE Trans-actions on Neural Systems and Rehabilitation Engineering, [see also IEEE Trans. on Rehabilitation Engineering (2005), 160-165.

Holsheimer, J. , et al., "Chronaxie calculated from current-duration and voltage-duration data", J Neurosci Methods 97(1). (Apr. 1, 2000),45-50.

Hines, M. L., et al., "The Neuron simulation environment", Neural Comput. 9(6). (Aug. 15, 1997), 1179-209.

Herzog, J., et al., "Most effective stimulation site in subthalamic deep brain stimulation for Parkinson's disease", Mov Disord. 19(9). (Sep. 2004),1050-4.

Hershey, T., et al., "Cortical and subcortical blood flow effects of subthalamic nucleus stimulation in PD.", Neurology 61(6). (Sep. 23, 2003),816-21.

Hemm, S. , et al., "Evolution of Brain Impedance in Dystonic Patients Treated by GPi Electrical Stimulation", Neuromodulation 7(2) (Apr. 2004),67-75.

Hemm, S., et al., "Deep brain stimulation in movement disorders: stereotactic coregistration of two-dimensional electrical field modeling and magnetic resonance imaging.", J Neurosurg. 103(6): (Dec. 2005),949-55.

Haueisen, J, et al., "The influence of brain tissue anisotropy on human EEG and MEG", Neuroimage 15(1) (Jan. 2002),159-166.

Haslinger, B., et al., "Frequency-correlated decreases of motor cortex activity associated with subthalamic nucleus stimulation in Parkinson's disease.", Neuroimage 28(3). (Nov. 15, 2005),598-606.

Hashimoto, T. , et al., "Stimulation of the subthalamic nucleus changes the firing pattern of pallidal neurons", J Neurosci. 23(5). (Mar. 1, 2003),1916-23.

Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.

McNaughtan et al., "Electrochemical Issues in Impedance Tomography", 1st World Congress on Industrial Process Tomography, Buxton, Greater Manchester, Apr. 14-17, 1999.

Grill, WM., et al., "Electrical properties of implant encapsulation tissue", Ann Biomed Eng. vol. 22. (1994),23-33.

Grill, W. M., et al., "Deep brain stimulation creates an informational lesion of the stimulated nucleus", Neuroreport. 1517t (May 19, 2004 ), 1137-40.

International Search Report and Written Opinion for PCT Application No. PCT/US2022/032349 mailed Sep. 6, 2022.

Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015, 21(4):378-82.

Benoit M. Dawant et al: "The VU-DBS project: integrated and computer-assisted planning, intra-operative placement, and post-operative programming of deep-brain stimulators", Proceedings of SPIE, vol. 6509, Mar. 6, 2007 (Mar. 6, 2007), 11 pages.

METHODS AND SYSTEMS FOR DETERMINING AND USING AN INTENSITY INDEX FOR ELECTRICAL STIMULATION

CROSS-REFERENCE TO RELATED APPLICATIONS

This application claims the benefit under 35 U.S.C. § 119(e) of U.S. Provisional Patent Application Ser. No. 63/288,357, filed Dec. 10, 2021, which is incorporated herein by reference.

FIELD

The present disclosure is directed to the area of implantable electrical stimulation systems and methods of making and using the systems. The present disclosure is also directed to methods and systems for determining and using an intensity index for an implantable electrical stimulation system.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Deep brain stimulation can be used to treat a variety of diseases and disorders.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is a method for determining an intensity index for electrical stimulation. The method includes receiving stimulation information; determining a stimulation field from the stimulation information; determining at least one stimulation field function using the stimulation field; and analyzing the determined at least one stimulation field function to determine the intensity index. The intensity index corresponds to a stimulation target and indexes at least one dosing reference for electrical stimulation for that stimulation target.

In at least some aspects, determining the at least one stimulation field function and analyzing the determined at least one stimulation field function include determining a plurality of the stimulation field functions using the stimulation field and analyzing the determined stimulation field functions to determine the intensity index.

In at least some aspects, analyzing the determined at least one stimulation field function includes analyzing the determined at least one stimulation field function to identify the stimulation target and determining the intensity index from the identified stimulation target. In at least some aspects, the method further includes displaying, for a user, the stimulation target. In at least some aspects, displaying the stimulation target includes coloring or shading the stimulation target, where the coloring or shading highlights the stimulation target or indicates a confidence in the identification of the stimulation target.

In at least some aspects, the at least one stimulation field function is selected from a first derivative, or first difference, of the stimulation field, a second derivative, or second difference, of the stimulation field, or a driving function of the stimulation field. In at least some aspects, determining the at least one stimulation field function includes determining at least one of the at least one stimulation field function along a first trajectory. In at least some aspects, the first trajectory is a trajectory extending along a neural element, anatomical structure, astrocyte, microglia, or oligodendrocyte.

In at least some aspects, analyzing the determined stimulation field function includes analyzing the determined stimulation field function using at least one threshold condition or conditional statement regarding the determined at least one stimulation field function. In at least some aspects, the at least one stimulation field function includes a first stimulation field function and a second stimulation field function, wherein the at least threshold condition or conditional statement includes a comparison between values of first and second stimulation field functions.

In at least some aspects, analyzing the determined at least one stimulation field function includes analyzing the determined at least one stimulation field function at one or more observational points. In at least some aspects, the method further includes receiving a user selection of at least one of the one or more observational points. In at least some aspects, at least one of the one or more observational points is a center, or centroid of mass, of the stimulation field. In at least some aspects, at least one of the one or more observational points is a region, wherein analyzing the determined at least one stimulation field function at the one or more observational points includes obtaining a maximum or minimum value of at least one of the at least one stimulation field function over the region. In at least some aspects, the at least one stimulation field functions includes a first stimulation field function and a second stimulation field function and the one or more observational point includes at least one first observational point and at least one second observational point, wherein analyzing the determined at least one stimulation field function at the one or more observational points includes analyzing the first stimulation field function at the at least one first observational point and analyzing the second stimulation field function at the at least one second observational point.

Another aspect is a method for determining an intensity index for electrical stimulation. The method includes receiving stimulation information; comparing the stimulation information to a plurality of predetermined stimulation fields, predetermined stimulation instances, or predetermined stimulation geometries, where each of the predetermined stimulation fields, predetermined stimulation instances, or predetermined stimulation geometries is associated with one of a plurality of intensity indices, where each of the intensity indices corresponds to a stimulation target and indexes at least one dosing reference for electrical stimulation for that stimulation target; and, when the comparison indicates that the stimulation information matches one of the predetermined stimulation fields, predetermined stimulation instances, or predetermined stimulation geometries within a threshold condition, determining that the intensity index for the stimulation information corresponds to the intensity index associated with the matched one of the predetermined stimulation fields, predetermined stimulation instances, or predetermined stimulation geometries.

In at least some aspects, the method further includes, when the comparison indicates that the stimulation information does not match any of the predetermined stimulation fields, predetermined stimulation instances, or predetermined stimulation geometries within a threshold condition: determining a stimulation field from the stimulation information; determining at least one stimulation field function using the stimulation field; and analyzing the determined at least one stimulation field function to determine the intensity index for the stimulation information. Any of the other aspects described above can also be included.

In at least some aspects, the comparing includes performing a correlation, similarity, or difference assessment between the stimulation information and the predetermined stimulation fields, predetermined stimulation instances, or predetermined stimulation geometries.

Any of the methods describe above can also include electrically stimulating a patient and adjusting the stimulation in accordance with the intensity index.

Yet another aspect is a system for determining an intensity index for electrical stimulation. The system includes at least one processor configured to perform actions, including any of the methods described above.

A further aspect is a non-transitory computer-readable medium having processor-executable instructions for estimating neural activation arising from stimulation by a stimulation system, the processor-executable instructions when installed onto a device enable the device to perform actions, the actions including any of the methods described above.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
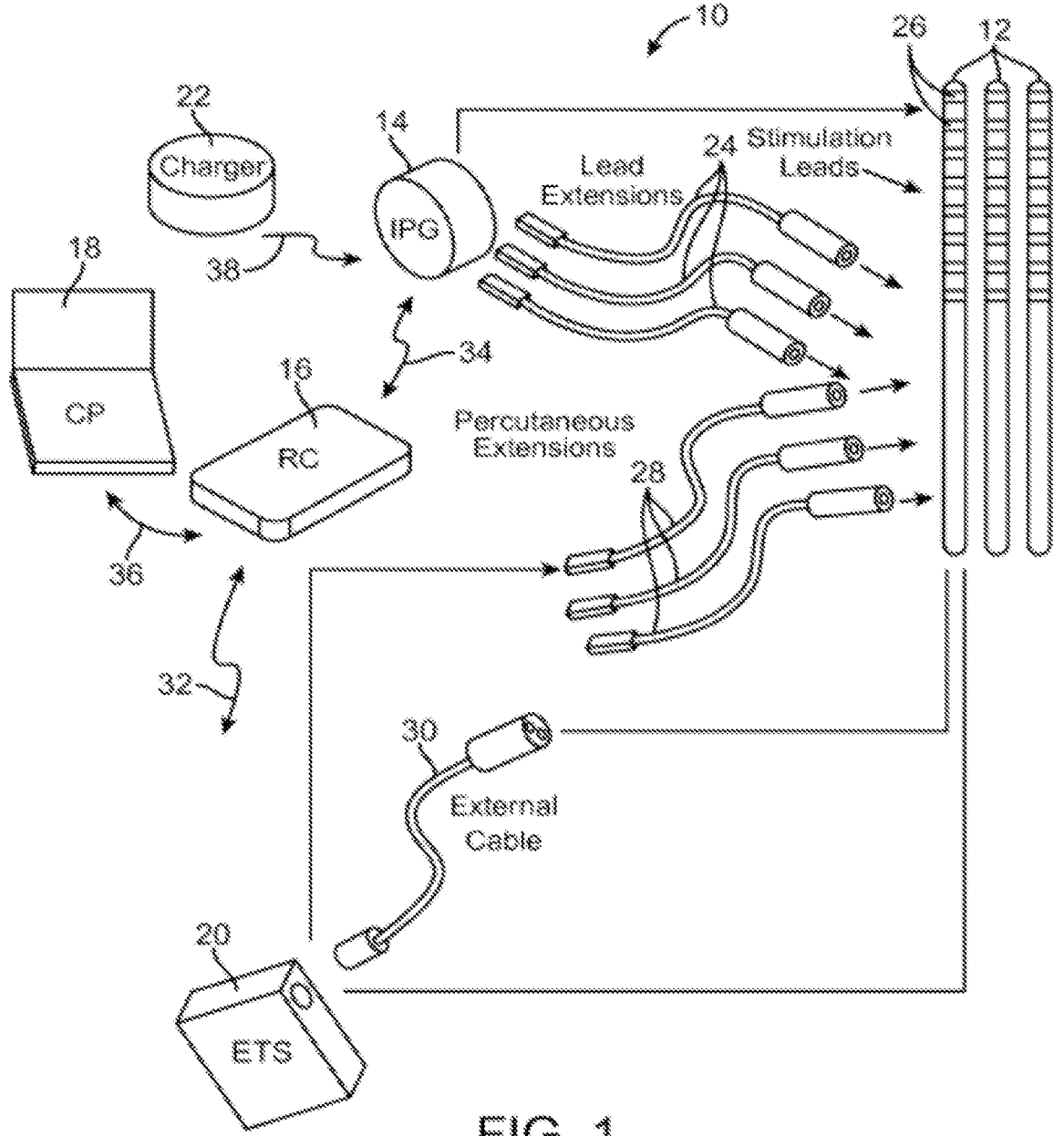
FIG. 1 is a schematic view of one embodiment of an electrical stimulation system.

The present disclosure is directed to the area of implantable electrical stimulation systems and methods of making and using the systems. The present disclosure is also directed to methods and systems for determining and using an intensity index for an implantable electrical stimulation system.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741, 892; 7,244,150; 7,450,997; 7,672,734; 7,761,165; 7,783, 359; 7,792,590; 7,809,446; 7,949,395; 7,974,706; 8,175, 710; 8,224,450; 8,271,094; 8,295,944; 8,364,278; 8,391, 985; and 8,688,235; and U.S. Patent Applications Publication Nos. 2007/0150036; 2009/0187222; 2009/ 0276021; 2010/0076535; 2010/0268298; 2011/0005069; 2011/0004267; 2011/0078900; 2011/0130817; 2011/ 0130818; 2011/0238129; 2011/0313500; 2012/0016378; 2012/0046710; 2012/0071949; 2012/0165911; 2012/ 0197375; 2012/0203316; 2012/0203320; 2012/0203321; 2012/0316615; 2013/0105071; and 2013/0197602, all of which are incorporated herein by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, or peripheral nerve stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. Examples of leads with segmented electrodes include U.S. Pat. Nos. 8,473,061; 8,571,665; and 8,792,993; U.S. Patent Application Publications Nos. 2010/0268298; 2011/ 0005069; 2011/0130803; 2011/0130816; 2011/0130817; 2011/0130818; 2011/0078900; 2011/0238129; 2012/ 0016378; 2012/0046710; 2012/0071949; 2012/0165911; 2012/0197375; 2012/0203316; 2012/0203320; 2012/ 0203321; 2013/0197424; 2013/0197602; 2014/0039587; 2014/0353001; 2014/0358208; 2014/0358209; 2014/ 0358210; 2015/0045864; 2015/0066120; 2015/0018915; and 2015/0051681, all of which are incorporated herein by reference.

For illustrative purposes, the systems and leads are described herein relative to use for spinal cord stimulation, but it will be understood that any of the leads can be used for applications other than spinal cord stimulation, including deep brain stimulation, peripheral nerve stimulation, dorsal root ganglion stimulation, sacral nerve stimulation, or stimulation of other nerves, muscles, and tissues.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22. The IPG and ETS are examples of control modules for the electrical stimulation system.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity or at any other suitable site. The implantable pulse generator can have multiple stimulation channels which may be independently programmable to control the magnitude of the current stimulus from each channel. In some embodiments, the implantable pulse generator can have any suitable number of stimulation channels including, but not limited to, 4, 6, 8, 12, 16, 32, or more stimulation channels. The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated herein by reference.

It will be recognized that an electrical stimulation system can include one, two, three, or more implanted leads with each lead having one or more (for example, 4, 8, 16, 32, or more) electrodes. Each lead can be a percutaneous lead, paddle lead, cuff lead, or any other suitable arrangement of electrodes. The electrodes can be ring electrodes, segmented electrodes, tip electrodes, or electrodes having any other suitable size or shape. For example, a paddle lead may have electrodes with a square, rectangular, oval, circular, or any other suitable shape with some of these shapes have sharp or rounded corners. Examples of percutaneous leads with or without segmented electrodes can be found at, for example, U.S. Pat. Nos. 9,149,630; 9,289,596; 9,381,348; 9,498,620; and 9,566,596. Examples of paddles leads can be found at, for example, U.S. Pat. Nos. 8,774,941; 9,061,138; 9,162, 056; 9,289,600; 9,327,111; and 9,492,655. Examples of cuff leads can be found at, for example, U.S. Pat. Nos. 10,485, 969; 10,493,269; and 10,814,127. All of the patents cited in this paragraph are incorporated herein by reference in their entireties.

Electrical stimulation using one or more electrodes produces an electrical field that can affect stimulation targets, such as neural elements, within the electrical field. The electrical stimulation, and resulting stimulation field, is generated by selection of a number of different stimulation parameters such as, for example, electrode selection (e.g., one or more selected electrodes), polarity (anode or cathode), stimulation amplitude (for each selected electrode), pulse width (e.g., pulse duration), pulse rate, pulse shape (for example, pulse phases or active/passive charging/discharging), or the like or any combination thereof. The electrical stimulation can be monopolar, bipolar, tripolar, or any other multi-polar arrangement. When programming an electrical stimulation system to provide therapeutic electrical stimulation, a clinician, stimulation programmer, or other individual (or a partially or fully automated system) can vary each (or a subset) of the stimulation parameters to produce a suitable (or optimal) therapy. Such programming can be time consuming due to the multi-variable nature of the stimulation.

Moreover, it is found that stimulation fields (e.g., a particular selection of stimulation parameters) can affect different stimulation targets, such as neural elements, in different ways. For example, in at least some instances, axons of passage are particularly sensitive to the second spatial derivative of a stimulation field in a direction parallel to the axons. In contrast, in at least some instances, neural terminals and dendrites are particularly sensitive to the first spatial derivative of the stimulation field. Non-neuronal elements, such as astrocytes, microglia, and oligodendrocytes in the spinal cord, satellite ganglion cells in the dorsal root ganglia (DRG), or Schwann Cells in the periphery, may also experience differential effects dependent on stimulation field orientation.

A dosing reference (for example, a dosing curve, dosing paradigm, or dosing strategy) can represent the response (for example, an expected response, a measured response, or an average response) of a particular stimulation target to changes in one or more stimulation parameters, such as, for example, stimulation amplitude, pulse width, pulse rate, pulse shape, or the like or any combination thereof. Given the different effects of a stimulation field on different stimulation targets, the dosing references can be expected to differ between stimulation targets. The dosing reference may also depend on other elements such as the orientation of the stimulation targets, biophysical characteristics of the stimulation targets, selection of electrode(s), or the like or any combination thereof.

Dosing references can be determined empirically, experimentally, computationally, theoretically, using a machine learning algorithm or methodology (for example, using neural networks, regression modeling, support vector machines, data clustering, or the like or any combination thereof), or the like or any combination thereof. Dosing references may be patient-specific or may be universal or determined from a group of patients or from a selected population of patients (for example, a population of patients with similar age, health, gender, race/ethnicity, etiology, disease/disorder, or the like or any combination thereof) Dosing references may depend on the stimulation modality or strategy, such as, for example, regular or irregular stimulation, above- or below-perception stimulation, rapid onset and offset or slower onset and offset, or the like or any combination thereof.

An intensity index can be defined for any stimulation target, such as a neural or anatomical element, and can index one or more dosing references for that stimulation target. A system can include multiple intensity indices for stimulation of different stimulation targets. For example, a spinal cord stimulation system may include intensity indices for two or more of the following stimulation targets: location-defined targets such as the dorsal column, dorsal horn, dorsal root, dorsal root ganglia, or the like or any combination thereof or function-defined targets, such as excitatory, inhibitory, or projection neurons; structure-defined targets such as the cell body, axon, dendrites, terminals, or synapses; or the like or any combination thereof. A particular intensity index is selected to correspond to the desired stimulation target and indexes one or more dosing references selected for that stimulation target. In at least some embodiments, an intensity index may correspond to two or more stimulation targets (e.g., neural or anatomical elements) and represent one or more dosing references selected for those two or more stimulation targets. In at least some embodiments, the system or user selects an intensity index depending on the stimulation target (e.g., the neural or anatomical element(s) that is/are the target of the stimulation.)

Figure 3:
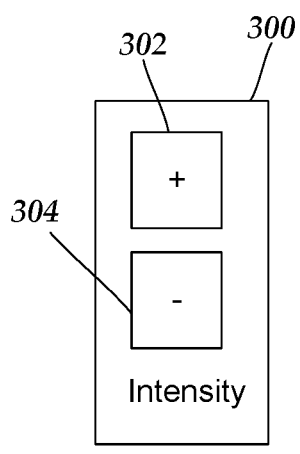
FIG. 3 illustrates a portion of a user interface with controls for increasing or decreasing an intensity of electrical stimulation.

In at least some embodiments, an electrical stimulation system can utilize an intensity parameter that a user (such as a clinician, stimulation programmer, or patient) can reliably increase or decrease stimulation by increasing or decreasing the intensity parameter instead of (or in addition to) modifying individual stimulation parameters. As the intensity parameter is changed, a processor and associated software of the system (for example, the CP 18, RC 16, ETS 20, or IPG 14 or any combination thereof) modifies one or more stimulation parameters (for example, stimulation amplitude, pulse width, pulse rate, pulse shape, electrode selection, or the like or any combination thereof) to increase or decrease the intensity of the stimulation. The modification of the stimulation parameters generated by increasing or decreasing the intensity parameter depends on the intensity index selected for the stimulation. Thus, increasing or decreasing the intensity parameter will produce different modifications of the stimulation parameter(s) depending on the selected intensity index. FIG. 3 illustrates a portion of one embodiment of a user interface 300 with intensity controls 302, 304 for increasing or decreasing, respectively, the intensity parameter based on the intensity index.

It will be understood that the terms "intensity parameter" and "intensity index" can be substituted with different terms that provide the same functionality as described herein. In at least some embodiments, the "intensity index" can by synonymous with a dosing reference or a set of dosing references or can by synonymous with a stimulation target. In at least some embodiments, the modifications to the stimulation parameters by adjusting the intensity parameter can be a function of two or more stimulation parameters such as, for example, stimulation amplitude, pulse width, or pulse rate. In at least some embodiments, the modifications to the stimulation parameters by adjusting the intensity parameter, for a given intensity index, can be determined empirically, experimentally, computationally, theoretically, using a machine learning algorithm or methodology (for example, using neural networks, regression modeling, support vector machines, cluster analysis based on patient input or the like or any combination thereof), or the like or any combination thereof. In at least some embodiments, the modifications to the stimulation parameters by adjusting the intensity parameter may be provided or stored in any suitable form including, but not limited to, one or more equations, one or more look-up tables, one or more graphs or charts, processor calculations, or the like or any combination thereof.

In at least some embodiments, the user or system selects an intensity index which then informs the system how to modify the stimulation parameters as the intensity parameter is adjusted. However, the intensity index (as well as the modifications that occur with adjusting the intensity parameter) can depend on the neural or anatomical element(s) that is/are the stimulation target. As an example, for spinal cord stimulation, there can be different intensity indices for different anatomical structures such as the dorsal column, the dorsal horn, the dorsal roots, or the dorsal root ganglia by lamina; or for different target cells by function or type (for example, neurons vs. glia); or for different neural structures such as the cell body, axon, dendrites, terminals, synapses, or the like.

Users of an electrical stimulation system may not be sufficiently knowledgeable to manually select the appropriate intensity index. As described herein, an electrical stimulation system (for example, the CP 18, RC 16, ETS 20, or IPG 14 or any combination thereof) can evaluate stimulation information provided by a user to determine and then suggest or select an intensity index. Examples of stimulation information provided by the user can include, but are not limited to, the selection of electrode(s) and the resulting electrode geometry; the selections of values for one or more other stimulation parameters; the identification of a stimulation region, stimulation field, or stimulation purpose; desired effect (for example, activation or inhibition), desired effect level (for example, supra-perception or sub-perception or having an action potential or compound action potential above or below certain level), the presence or absence of clinical side effects, patient preference or non-preference, or the like or any combination thereof. Although the embodiments described herein are directed to identifying or selecting the intensity index, it will be understood that, instead of identifying or selecting the intensity index, one or more dosing references can be identified or selected. Therefore, the term "intensity index" can be replaced by "one or more dosing curves" or "one or more dosing reference" in the description below.

Figure 2:
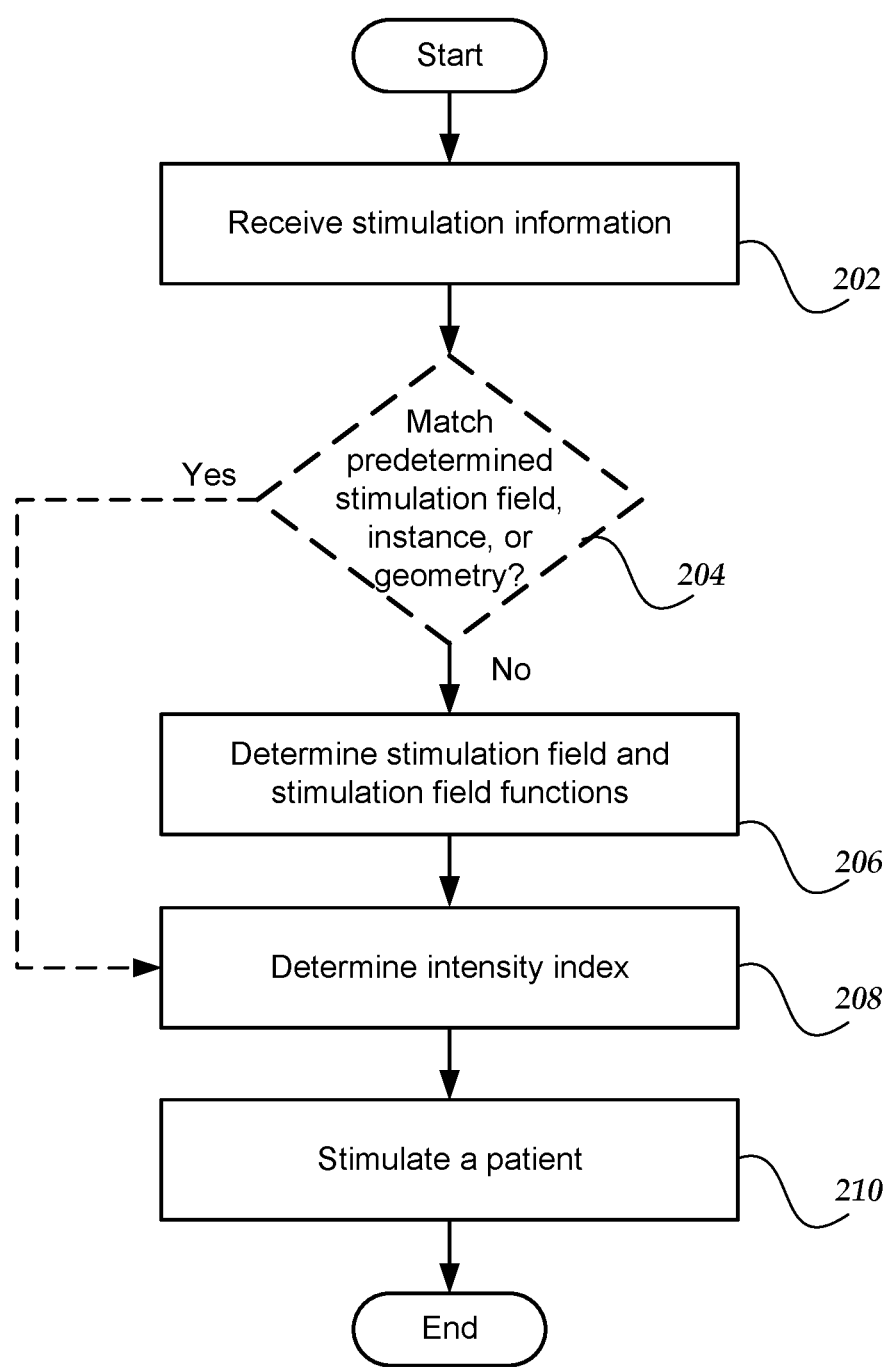
FIG. 2 is a flowchart of one embodiment of a method for determining a stimulation target or intensity index.

FIG. 2 illustrates one embodiment of a method for determining (e.g., identifying or selecting) an intensity index based on user input. In step 202, the user inputs or otherwise specifies stimulation information, such as, for example, an initial electrode selection, a stimulation geometry, values for one or more stimulation parameters, a target stimulation region or site, a target stimulation field, a stimulation or therapeutic purpose, desired effect (for example, activation or inhibition), desired effect level (for example, supra-perception or sub-perception or having an action potential or compound action potential above or below certain level), the presence or absence of clinical side effects, patient preference or non-preference, or the like or any combination thereof. Other items may be suitable stimulation information. In at least some instances, an initial electrode selection may also partially or fully define the stimulation geometry. In at least some instances, a specification of a stimulation geometry may partially or fully define an initial electrode selection.

As an example, the user may indicate a site of implantation, such as, for example for spinal cord stimulation, a thoracic or lumbar site or a specific spinal cord level or set of levels (for example, T7 or T9/T10). In at least some embodiments, a stimulation geometry may be specified by, for example, the number of stimulation regions (for example, stimulation regions that may be spatially or temporally separated), the span of the stimulation region (for example, the distance between the distal-most selected electrode and the proximal-most selected electrode), the extent of the desired stimulation effect (for example, the estimated area or volume of activation), or the number or strength of the anode(s) and cathode(s) (for example, if the stimulation is monopolar, bipolar, tripolar, or another multi-polar arrangement).

In at least some embodiments, information about the fractionalization of the stimulation amplitude can be used in combination with the electrode selection.

Fractionalization refers to the distribution of the stimulation amplitude among the selected electrodes. For example, if electrodes 2 and 4 are selected as cathodes and electrode 3 is selected as an anode, the cathodic stimulation amplitude could be distributed in a number of different ways (i.e., fractionalizations) among electrodes 2 and 4 including, but not limited to, 50% of the cathodic stimulation amplitude on each electrode, 67% on one electrode and 33% on the other electrode, 75% on one electrode and 25% on the other electrode, and so on.

In optional step 204, the system determines whether the user-provided information (for example, an electrode selection or stimulation geometry) matches (e.g., corresponds to, or resembles) a predetermined stimulation field, predetermined stimulation instance, or predetermined stimulation geometry within a threshold condition. In at least some embodiments, each of the predetermined stimulation fields, predetermined stimulation instances, or predetermined stimulation geometries is assigned to a specific intensity index or specific stimulation target. In at least some embodiments, each of the predetermined stimulation field, predetermined stimulation instance, or predetermined stimulation geometry can be based on, for example, calculations, previous stimulation of the same patient or different patient(s), typical programming practices or configurations, or the like or any combination thereof.

The determination may include, for example, matching the stimulation information using a look-up table; comparing the features of the user-provided information (for example, the selection of electrodes or the fractionalization (e.g., distribution) of the stimulation amplitude over the selected electrodes); performing a correlation or comparison assessment; or performing an assessment whether the stimulation information differs (for example, in area, volume, one or more stimulation parameter values, or the like or any combination thereof) from the predetermined stimulation field, predetermined stimulation instance, or predetermined stimulation geometry by no more than a threshold amount (for example, 1, 2, 5, or 10%). Any suitable mechanism for performing the assessments or comparisons can be used including, but not limited to, percent deviation, mean square error analysis or outlier detection or other difference determinations; overlap, correlation, pattern recognition, clustering, or other similarity assessments or assessments of variance; machine learning techniques; or the like or any combination thereof. Any suitable threshold condition can be used including, but not limited to, an amount or percentage of difference, an amount of overlap, or the like or any combination thereof.

If the answer to the query in optional step 204 is yes, the process continues directly to step 208. If no, the process continues to step 206. As indicated, step 204 is optional and, if absent, step 206 follows step 202.

In step 206, the system determines one or more stimulation field functions at one or more points within the stimulation field. In at least some embodiments, the system determines or calculates the stimulation field (or an approximation of the stimulation field) using the stimulation information from the user. The terms "stimulation field", "stimulation field map" (SFM), "volume of activation" (VOA), or "volume of tissue activated (VTA)" are often used to designate an estimated region of tissue that will be stimulated for a particular set of stimulation parameters. Any suitable method for determining the VOA/SFM/VTA can be used including, but not limited to, those described in, for example, U.S. Pat. Nos. 8,326,433; 8,675,945; 8,831,731; 8,849,632; 8.958,615; and 10,265,528; U.S. Patent Application Publications Nos. 2009/0287272; 2009/0287273; 2012/0314924; 2013/0116744; 2014/0122379; and 2015/0066111, all of which are incorporated herein by reference.

In at least some other embodiments, a selection of stimulation fields are pre-computed and a look-up table or stimulation field matching is used to determine a pre-computed stimulation field that corresponds to the stimulation information provided by the user. In at least some embodiments, interpolation may be used to modify the pre-computed stimulation field to more closely correspond to the stimulation information provided by the user. In yet other embodiments, the stimulation field is determined based on measurements obtained from the tissue before, during, or after stimulation or any combination thereof. Any combination of these methods or techniques for determining the stimulation field can be used.

In at least some embodiments, the stimulation field is calculated, determined, or selected to be a three-dimensional volume. In at least some embodiments, the stimulation field is calculated, determined, or selected to be one or more two-dimensional planes (for example, planes that intersect the electrodes of the lead(s), the surface of the spinal cord, or the tissue depth at or within which the stimulation target is located).

In at least some embodiments, the stimulation field is determined or calculated at multiple points. The points can be points of a grid or any other arrangement of points. In at least some embodiments, the density of the points in any particular region may be uniform or may depend on factors such as, for example, anatomical features of the region, user-selected target regions, anatomical features of the stimulation target (for example, orientation, location of dendritic trees or axon projections, or the like) or the like or any combination thereof.

In at least some embodiments, the grid of points over which the stimulation field is calculated or otherwise determined can be selected (entirely or in part) to resemble a specific anatomical target (for example, a neural or anatomical target) that is in (or partially within) the region of stimulation. For example, for spinal cord stimulation, the grid of points may resemble the spinal cord itself, the dorsal horns, the dorsal column, or other anatomical features or elements of the spinal cord or associated neural or anatomical elements.

In at least some embodiments, the system may allow a user to specify the spacing, depth, or orientation of these points. Such system controls may also be included in other embodiments of the system including those that use a regular grid of points. In at least some embodiments, the system may also allow the user to identify specific points for the grid.

One or more stimulation field functions are determined at one or more observational points (described below) using the stimulation field. In at least some embodiments, the system determines and calculates only a portion of the stimulation field in order to determine the stimulation field function(s) at one or more observational points within the stimulation field.

Examples of stimulation field functions include, but are not limited to, the first derivative (or first difference) of the stimulation field along a direction or trajectory such as, for example, $dV_x/dx$ or $dV_z/dz$; the second derivative (or second difference) of the stimulation field along a direction or trajectory such as, for example, $d^2V_x/dx^2$ or $d^2V_z/dz^2$; a driving function such as, for example, $(\Sigma\phi d^2Vx)$ or $(\Sigma\phi d^2V_z)$, respectively; or the like or any combination thereof. The identified driving function is a weighted (with weight $\phi$ which may be dependent on pulse width or other variables) summation of the second derivative at selected points along an axon, dendrite, or other neural or anatomical element. Examples of the driving function can be found in Warmen et al., IEEE Trans Biomed Eng. 1992; 39:1244-54 which is incorporated herein by reference in its entirety. The specific stimulation field functions identified above are merely examples. It will be understood that any of the stimulation field functions can be modified by substituting x or z with x, y, z, any other direction (which can be any linear or non-linear direction), or time (t). One example is a first derivative defined as $dV_x/dr$, where r is a linear or non-linear direction.

In step 208, the system determines (e.g., identifies or selects) the intensity index. In at least some embodiments, the system first determines the stimulation target and then the system determines an appropriate intensity index from the stimulation target.

As indicated above if the query in optional step 204 is yes, then the system determines the intensity index or stimulation target from the user-provided information that corresponds to, or resembles, a predetermined stimulation field, predetermined stimulation instance, or predetermined stimulation geometry. In at least some embodiments, each of the predetermined stimulation fields, predetermined stimulation instances, or predetermined stimulation geometries is assigned to a specific intensity index or specific stimulation target.

If the one or more stimulation field functions are determined in step 206, then the system analyzes the stimulation field function(s) to determine the intensity index or stimulation target. For example, the system may implement a decision tree or other decision-making procedure that utilizes one or more threshold conditions or conditional statements (or any combination thereof) that are tested. In at least some embodiments, the results of one or more of the threshold conditions or conditional statements can identify a stimulation target or intensity index.

Any suitable threshold conditions or conditional statements can be used. For example, a threshold condition could correspond to a threshold value of a stimulation field function or threshold values for multiple stimulation field functions. As another example, a conditional statement may include a comparison between values for two or more of the stimulation field functions.

The following is one example of conditional statements for determining a stimulation target or intensity index for spinal cord stimulation (using a coordinated system where the z axis extends along the spinal cord or the longitudinal axis of the lead and the x axis extends laterally between and beyond the dorsal horns): If $dV_z/dz$ is greater than either $d^2V_z/dz^2$ or $dV_x/dx$, then the stimulation target is a dorsal horn elements with target anatomical structure aligned in the z direction; if $d^2V_z/dz^2$ is greater than either $dV_z/dz$ or $dV_x/dx$, then the stimulation target is a dorsal column fiber/axon in the z direction; and if $dV_x/dx$ is greater than either $d^2V_z/dz^2$ or $dV_z/dz$, then the stimulation target is a dorsal root afferent or afferent terminals in the x direction. A suitable intensity index is selected for the indicated stimulation target.

The following is another example for spinal cord stimulation: If $dV_z/dz$ is greater than either $(\Sigma\phi d^2V_x)$, $\Sigma\phi d^2V_z)$, or $dV_x/dx$, then the stimulation target is a dorsal horn in the z direction; if $(\Sigma\phi d^2V_x)$ or $(\Sigma\phi d^2V_z)$ is greater than either $dV_z/dz$ or $dV_x/dx$, then the stimulation target is a dorsal column in the z direction; and if $dV_x/dx$ is greater than either $(\Sigma\phi d^2V_x)$, $(\Sigma\phi d^2V_z)$, or $dV_z/dz$, then the stimulation target is a dorsal root or afferent in the x direction. A suitable intensity index is selected for the indicated stimulation target.

It will be understood that these are just two examples. Any other suitable threshold condition(s) or conditional statement(s) can be used.

In at least some embodiments, the threshold condition(s) or conditional statement(s) can be tested at a single observational point or at multiple observational points. In at least some embodiments, a first stimulation field function at a first observational point can be compared to a second stimulation field function at a different second point. As an example, $d^2V_z/dz^2$ at the spinal midline may be compared to a $dV_x/dx$ at a dorsal root entry zone or $dV_z/dz$ at a dorsal root entry zone may be compared to a $dV_x/dx$ at the same dorsal root entry zone. In at least some embodiments, the different observational points can be used for estimating recruitment of different stimulation targets to determine the intended stimulation target.

The selection of observational point(s) can be arbitrary or can be made using any suitable criteria or selection methods such as those described below. When more than one threshold condition or conditional statement is tested or when more than one observational point is used for the testing, then the system can utilize any method for analyzing, selecting, combining, or scoring the results to obtain a final result used to determine the intensity index. In at least some embodiments, for multiple observational points for a particular threshold condition or conditional statement, the result obtained at the largest number of those observational points is used for determining the stimulation target or intensity index. In at least some embodiments, variation in the results of the threshold condition(s) or conditional statement(s) may be used to determine or estimate a reliability of, or confidence in, the final determination of the stimulation target or intensity index. In at least some embodiments, a reliability or confidence determination or estimate is reported to the user.

In at least some embodiments, the threshold condition(s) or conditional statement(s) are tested for one or more of trajectories at each observational point. In at least some embodiments, the trajectory(ies) can be selected arbitrarily or may be selected to, for example, extend along an anatomical feature or element (for example, along a dorsal horn or dorsal column or perpendicular to the dorsal horn or dorsal column). In at least some embodiments, the length of trajectory or resolution of observational points may be selected based on factors such as size or geometry of the neural or anatomical element. In at least some embodiments, the size, resolution, or geometry may be based on a model or may be input by a user. In at least some embodiments, one or more of the trajectories may be a non-Cartesian geometry such as, for example, a trajectory along a neural or anatomical element which may not be straight.

Any suitable observational point(s) can be used. In at least some embodiments, a suitable observational point can be a central point of stimulation, such as a center (or centroid of mass) of the stimulation field, a position equidistant from the lead and the edge of the stimulation field, a position between two leads, or the like. In at least some embodiments, an observational point may correspond to a region (for example, a boxed region) of the grid of points where the maximum (or minimum) value of the stimulation field function within the boxed region is taken as the value representative of the region (i.e., the observational point). In at least some embodiments, the user may select the site of one or more observational points. In at least some embodiments, an observational point may be selected as a center of the selected electrode configuration or the median or mean of the stimulation field. In at least some embodiments, one or more observational points may be selected to correspond to a particular anatomical feature or element.

In at least some embodiments, the observational points can be selected (entirely or in part) to resemble a specific anatomical target (for example, a neural target) that is in the region of stimulation. For example, for spinal cord stimulation, the observational points may resemble the spinal cord itself, the dorsal horns, the dorsal column, or other anatomical features or elements of the spinal cord or associated neural elements. In at least some embodiments, the system may also allow the user to identify specific observational points.

In at least some embodiments, the results of the threshold condition(s) or conditional statement(s) or values obtained for the stimulation field functions can be displayed for a user. In at least some embodiments, the displayed results or values can be sorted or ranked or the corresponding stimulation targets may be mapped with indication of ranking or any combination thereof. This can facilitate review by the user to confirm the determined stimulation target or intensity index. For example, for the two examples of sets of conditional statements describe above, the values for each of the stimulation field functions and the results of each of the conditional statements can be displayed for the user.

In at least some embodiments, color, shading, or any other suitable graphical differentiation can be used to represent the determined stimulation target or intensity index (and, optionally, stimulation targets or intensity indices that were not determined or selected.) In at least some embodiments, color, shading, or any other suitable graphical differentiation can be used to indicate the relative confidence in the selection or non-selection for different stimulation targets or the relative strength of the different stimulation targets for selection. For example, a darker shade of a color could indicate more confidence in the determination. In at least some embodiments, threshold values or conditions can be set by the user such that only a stimulation target or region with an index/score/rating that is beyond the value is displayed or colored/shaded.

In at least some embodiments, instead of (or in addition to) calculations of the stimulation field or stimulation field functions, the electrodes of the lead can be used as sensors to measure or determine the stimulation field or stimulation field functions. In at least some embodiments, the electrodes measure or determine the stimulation field or stimulation field functions between pulses of the stimulation or during any other quiescent periods. In at least some embodiments, the electrodes measure or determine the stimulation field or stimulation field functions during delivery of stimulation. In at least some of these embodiments, the electrodes delivering stimulation are not used as sensors. In at least some embodiments utilizing the electrodes as sensors, the observational points may be limited to the number of electrodes available for sensing. In at least some embodiments, the stimulation pulses may impact the sensing if not attenuated or otherwise de-amplified.

In step 210, a patient can be stimulated using an electrical stimulation system, such as the electrical stimulation system illustrated in FIG. 1. The intensity index can be used to define the modifications to the stimulation parameters as the intensity parameter is increased or decreased using controls such as those illustrated in FIG. 3.

Figure 4:
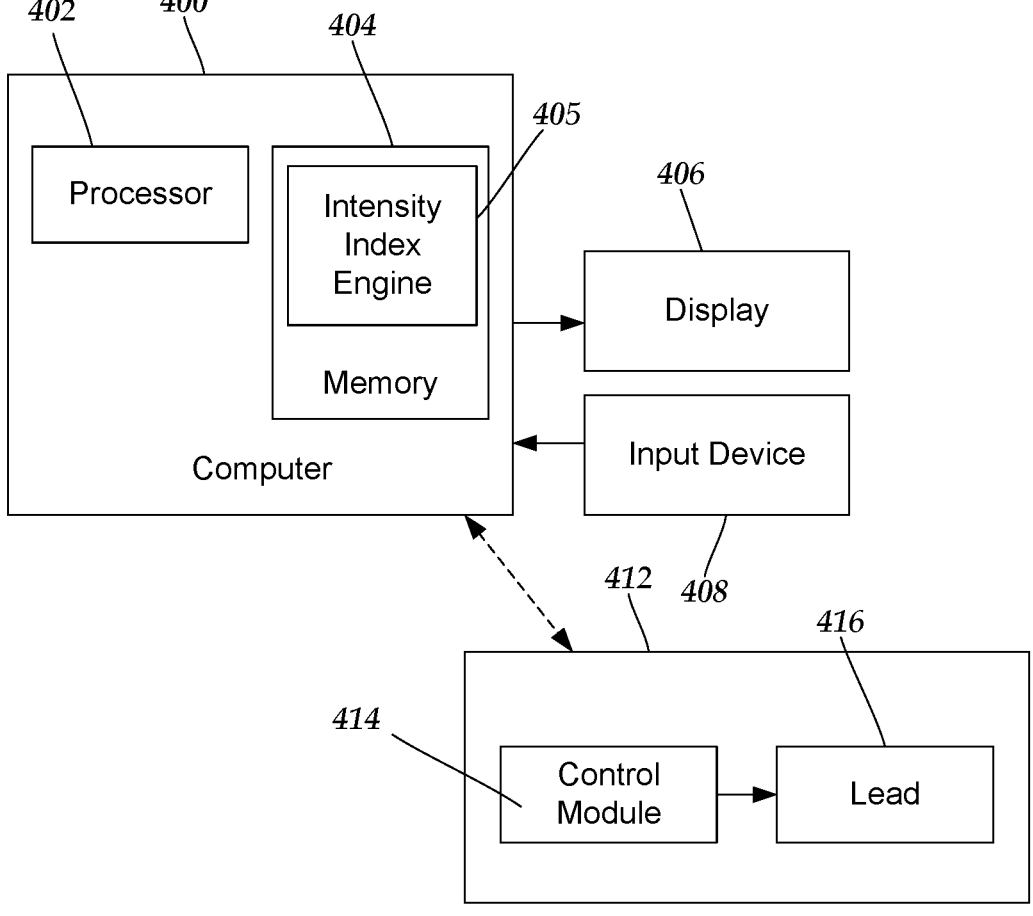
FIG. 4 is a schematic block diagram of a system for practicing the methods described herein.

FIG. 4 illustrates one embodiment of a system for practicing any of the methods described herein. The system can include a computer 400 or any other similar device that includes at least one processor 402 and a memory 404, a display 406, an input device 408, and, optionally, the electrical stimulation system 412.

The computer 400 can be a laptop computer, desktop computer, tablet, mobile device, smartphone, or other devices that can run applications or programs, or any other suitable device for processing information and for presenting a user interface. The computer can be, for example, the CP 18 or RC 16 of FIG. 1. The computer 400 can be local to the user or can include components that are non-local to the user including one or both of the processor 402 or memory 404 (or portions thereof). For example, in some embodiments, the user may operate a terminal that is connected to a non-local computer. In other embodiments, the memory can be non-local to the user. As another example, the computer 400 may utilize or communicate with a processor in the control module 414 (such as the IPG 4 or ETS 20 of FIG. 1).

The computer 400 can utilize any suitable processor 402 including one or more hardware processors that may be local to the user or non-local to the user or other components of the computer. The processor 402 is configured to execute instructions provided to the processor, as described below.

Any suitable memory 404 can be used for the processor 402. The memory 404 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

Residing in the memory 405 are instructions for an intensity index engine 405 which, when executed by the processor 402, determine the intensity index. The instructions of the intensity index engine 405 can correspond to any of the methods described above and, in particular, any of the embodiments of the method illustrated in FIG. 2 and described in the corresponding text related to FIG. 2.

The display 406 can be any suitable display device, such as a monitor, screen, display, or the like, and can include a printer. The input device 408 can be, for example, a keyboard, mouse, touch screen, track ball, joystick, voice recognition system, or any combination thereof, or the like and can be used by the user to interact with a user interface or clinical effects map.

The electrical stimulation system 412 can include, for example, a control module 414 (for example, the IPG 4 or ETS 20 of FIG. 1) and a lead 416 (for example, the lead 12 illustrated in FIG. 1.) The electrical stimulation system 412 may communicate with the computer 400 through a wired or wireless connection or, alternatively or additionally, a user can provide information between the electrical stimulation system 412 and the computer 400 using a computer-readable medium or by some other mechanism. In some embodiments, the computer 400 may include part of the electrical stimulation system. In at least some embodiments, the computer 400 can program the control module 414 for delivery of stimulation pulses, charge recovery pulse, charge recovery phases, or the like or any combination thereof.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A method for determining an intensity index for electrical stimulation, the method comprising:
   receiving stimulation information;
   determining a stimulation field from the stimulation information;
   determining at least one stimulation field function using the stimulation field;
   analyzing the determined at least one stimulation field function to determine the intensity index, wherein the intensity index corresponds to a stimulation target and indexes at least one dosing reference for electrical stimulation for that stimulation target, wherein the dosing reference represents the response of the stimulation target to changes in one or more stimulation parameters, wherein an intensity parameter alters delivery of therapy according to the intensity index and the intensity parameter is a function of at least two of stimulation amplitude, pulse width, pulse rate, or pulse shape;
   selecting a value of the intensity parameter for stimulating a patient; and
   stimulating a patient according to the selected value of the intensity parameter.

2. The method of claim 1, wherein determining the at least one stimulation field function and analyzing the determined at least one stimulation field function comprise determining a plurality of the stimulation field functions using the stimulation field and analyzing the determined stimulation field functions to determine the intensity index.

3. The method of claim 1, wherein analyzing the determined at least one stimulation field function comprises analyzing the determined at least one stimulation field function to identify the stimulation target and determining the intensity index from the identified stimulation target.

4. The method of claim 3, further comprising displaying, for a user, the stimulation target.

5. The method of claim 4, wherein displaying the stimulation target comprises coloring or shading the stimulation target, wherein the coloring or shading highlights the stimulation target or indicates a confidence in the identification of the stimulation target.

6. The method of claim 1, wherein the at least one stimulation field function is selected from a first derivative, or first difference, of the stimulation field, a second derivative, or second difference, of the stimulation field, or a driving function of the stimulation field.

7. The method of claim 6, wherein determining the at least one stimulation field function comprises determining at least one of the at least one stimulation field function along a first trajectory.

8. The method of claim 7, wherein the first trajectory is a trajectory extending along a neural element, anatomical structure, astrocyte, microglia, or oligodendrocyte.

9. The method of claim 1, wherein analyzing the determined at least one stimulation field function comprises analyzing the determined at least one stimulation field function using at least one threshold condition or conditional statement regarding the determined at least one stimulation field function.

10. The method of claim 9, wherein the at least one stimulation field function comprises a first stimulation field function and a second stimulation field function, wherein the at least threshold condition or conditional statement comprises a comparison between values of first and second stimulation field functions.

11. The method of claim 1, wherein analyzing the determined at least one stimulation field function comprises analyzing the determined at least one stimulation field function at one or more observational points.

12. The method of claim 11, further comprising receiving a user selection of at least one of the one or more observational points.

13. The method of claim 11, wherein at least one of the one or more observational points is a center, or centroid of mass, of the stimulation field.

14. The method of claim 11, wherein at least one of the one or more observational points is a region, wherein analyzing the determined at least one stimulation field function at the one or more observational points comprises obtaining a maximum or minimum value of at least one of the at least one stimulation field function over the region.

15. The method of claim 11, wherein the at least one stimulation field functions comprises a first stimulation field function and a second stimulation field function and the one or more observational point comprises at least one first observational point and at least one second observational point, wherein analyzing the determined at least one stimulation field function at the one or more observational points comprises analyzing the first stimulation field function at the at least one first observational point and analyzing the second stimulation field function at the at least one second observational point.

16. A non-transitory computer-readable medium having processor-executable instructions for estimating neural activation arising from stimulation by a stimulation system, the processor-executable instructions when installed onto a device enable the device to perform actions, the actions comprising the method of claim 1.

17. A system for determining an intensity index for electrical stimulation, the system comprising:

at least one processor configured to perform actions, comprising:

receiving stimulation information;

determining a stimulation field from the stimulation information;

determining at least one stimulation field function using the stimulation field;

analyzing the determined at least one stimulation field function to determine the intensity index, wherein the intensity index corresponds to a stimulation target and indexes at least one dosing reference for electrical stimulation for that stimulation target, wherein the dosing reference represents the response of the stimulation target to changes in one or more stimulation parameters, wherein an intensity parameter alters delivery of therapy according to the intensity index and the intensity parameter is a function of at least two of stimulation amplitude, pulse width, pulse rate, or pulse shape;

receiving a selection of a value of the intensity parameter associated with the intensity index for stimulating a patient; and directing stimulation of a patient according to the value of the intensity parameter.

\* \* \* \* \*